United States Patent
Imbert et al.

(10) Patent No.: US 8,798,940 B2
(45) Date of Patent: Aug. 5, 2014

(54) ROTATING ARRAY PROBE SYSTEM FOR NON-DESTRUCTIVE TESTING

(75) Inventors: Christophe Imbert, Quebec (CA); Michael Drummy, North Reading, MA (US)

(73) Assignee: Olympus NDT Inc., Waltham, MA (US)

( * ) Notice: Subject to any disclaimer, the term of this patent is extended or adjusted under 35 U.S.C. 154(b) by 586 days.

(21) Appl. No.: 13/083,648

(22) Filed: Apr. 11, 2011

(65) Prior Publication Data

US 2011/0257903 A1 Oct. 20, 2011

Related U.S. Application Data

(60) Provisional application No. 61/324,993, filed on Apr. 16, 2010.

(51) Int. Cl.
| | |
|---|---|
| *G01B 5/28* | (2006.01) |
| *G01N 29/275* | (2006.01) |
| *G01N 29/22* | (2006.01) |
| *G01M 13/04* | (2006.01) |
| *G01N 29/26* | (2006.01) |

(52) U.S. Cl.
CPC ............ *G01N 29/225* (2013.01); *G01N 29/275* (2013.01); *G01N 2291/2623* (2013.01); *G01M 13/045* (2013.01); *G01N 2291/2634* (2013.01); *G01N 29/262* (2013.01)
USPC .............................................. 702/35; 702/39

(58) Field of Classification Search
USPC ..................................................... 702/35, 39
See application file for complete search history.

(56) References Cited

U.S. PATENT DOCUMENTS

| 4,217,782 | A  * | 8/1980 | Pont ................................ 73/637 |
|---|---|---|---|
| 5,537,334 | A  * | 7/1996 | Attaoui et al. ................... 702/35 |
| 7,751,989 | B2 * | 7/2010 | Owens et al. ..................... 702/33 |
| 2004/0016139 | A1 * | 1/2004 | Lam et al. ......................... 33/544 |
| 2005/0182613 | A1 * | 8/2005 | Kwun et al. ...................... 703/18 |
| 2009/0132181 | A1 * | 5/2009 | Girndt ............................... 702/39 |
| 2010/0259252 | A1 * | 10/2010 | Kim et al. ...................... 324/240 |
| 2010/0307249 | A1 * | 12/2010 | Lesage et al. .................... 73/623 |

* cited by examiner

*Primary Examiner* — John Breene
*Assistant Examiner* — Manuel Rivera Vargas
(74) *Attorney, Agent, or Firm* — Ostrolenk Faber LLP

(57) ABSTRACT

A device is disclosed for performing non-destructive inspection and testing (NDT/NDI) of an elongated test object, wherein the inspection system includes: a test object conveyor for conveying the test object along a longitudinal conveyance path; a probe assembly including phased-array probes, the probe assembly being configured to induce signals in the test object and sense echoes reflected from the test object; a probe assembly conveyor configured to movably support the probe assembly, to move the probe assembly on a circumferential path about the test object; and a control system coupled to the test object conveyor and to the probe assembly conveyor and configured to allow data acquisition by and from the phased-array probes while, simultaneously, the test object moves along the longitudinal path and the phased-array probes move on the circumferential path. The test system may include phased-array probes of different types to optimize detecting faults or cracks in the test object which extend in different directions.

31 Claims, 13 Drawing Sheets

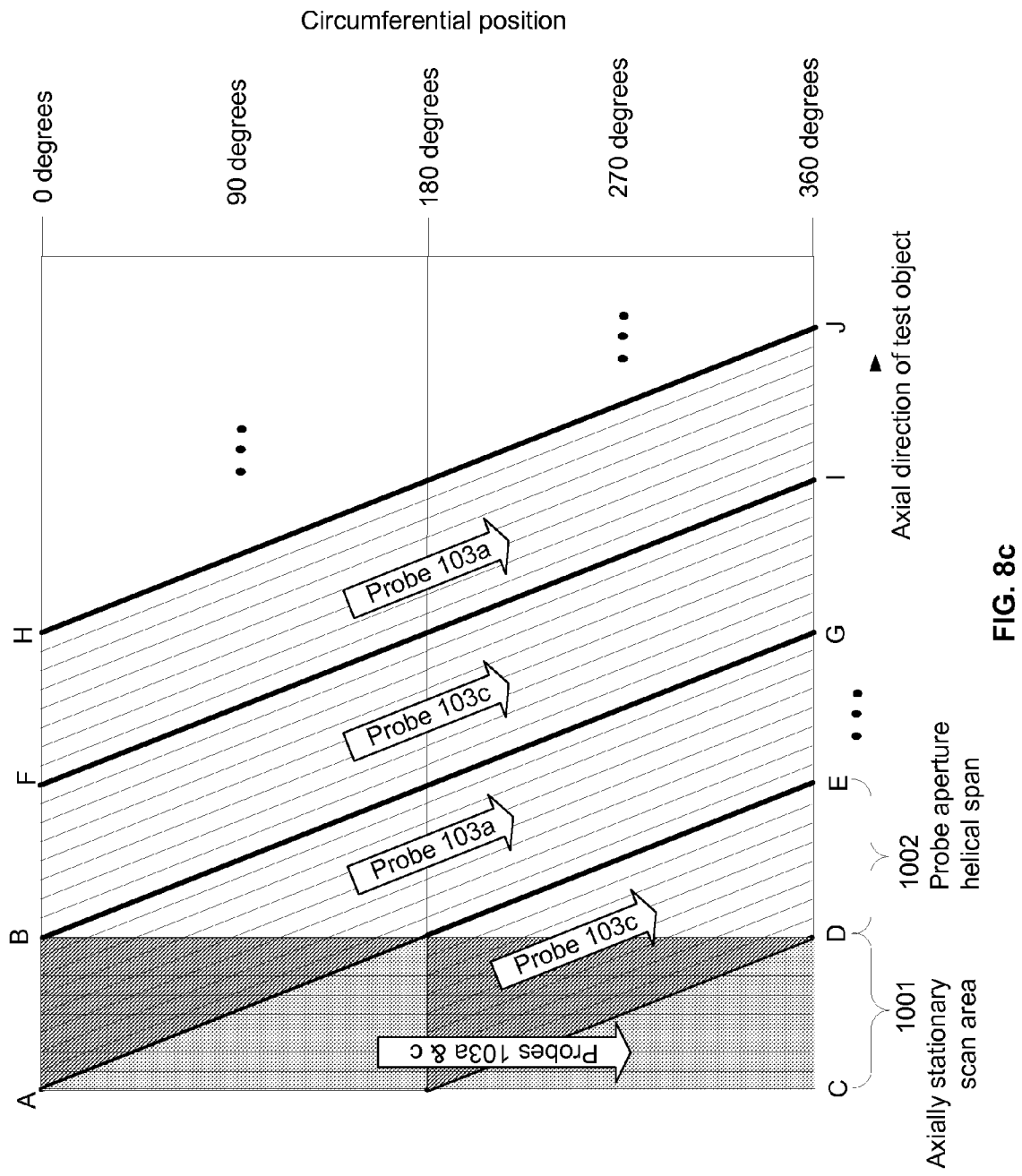

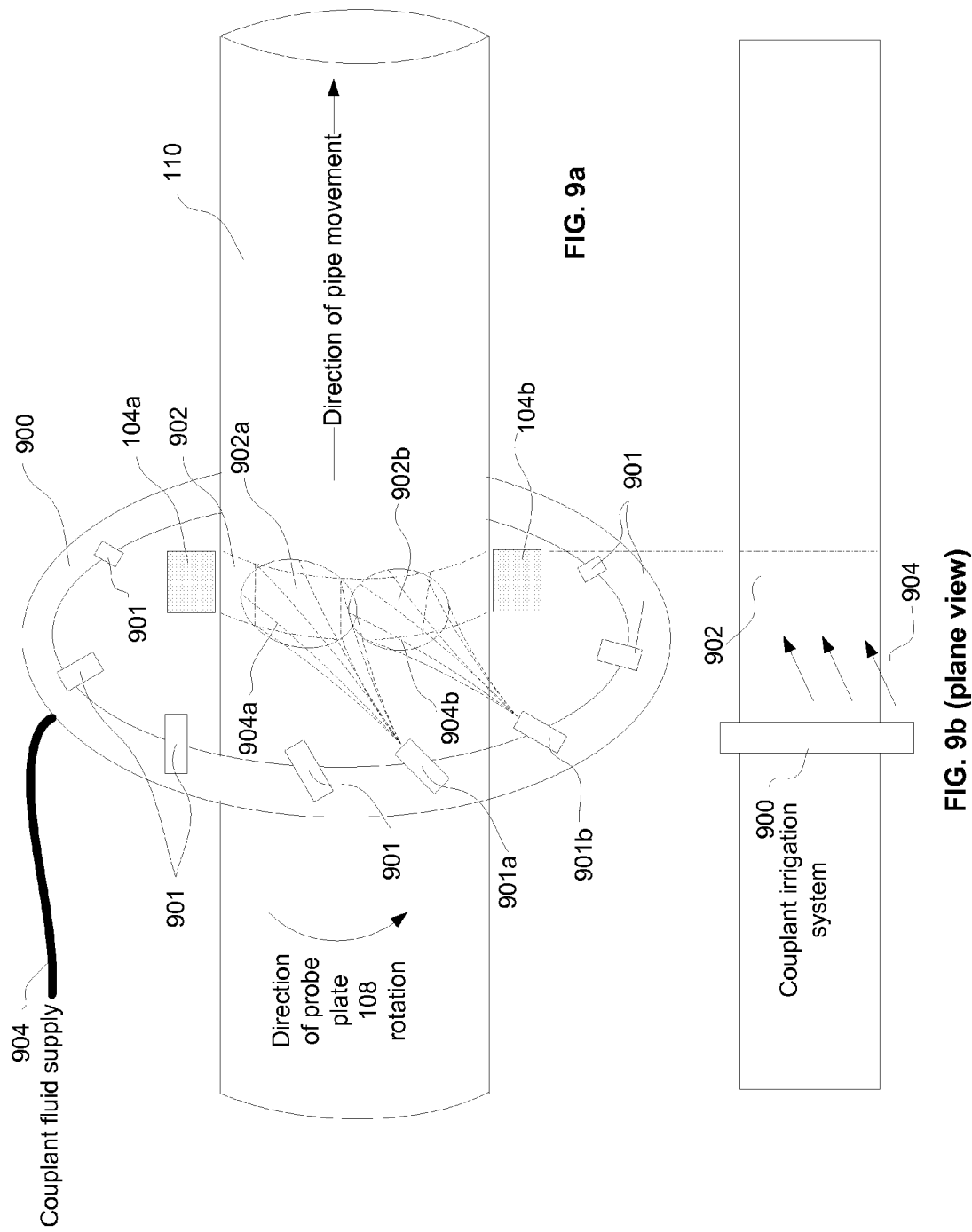

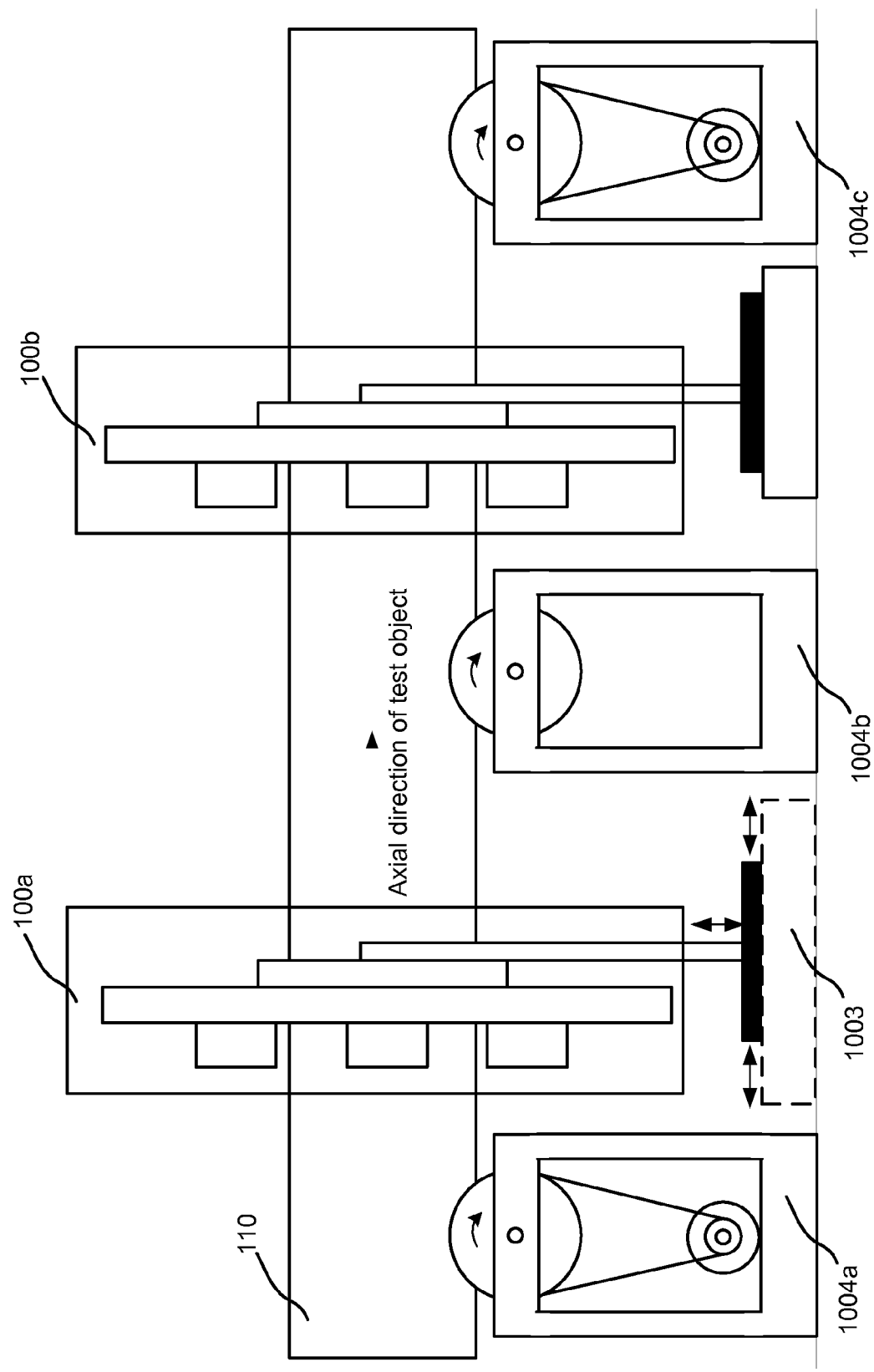

ROTATING ARRAY PROBE SYSTEM FOR NON-DESTRUCTIVE TESTING

CROSS-REFERENCE TO RELATED APPLICATIONS

This application claims the benefit and priority of U.S. Provisional patent application Ser. No. 61/324,993 filed Apr. 16, 2010 entitled ROTATING ARRAY PROBE NON-DESTRUCTIVE TEST SYSTEM FOR ENCIRCLED PIPE OR BAR INSPECTION, the entire disclosure of which is incorporated herein by reference.

FIELD OF THE INVENTION

The present invention relates to a non-destructive test and inspection (NDT/NDI) used to inspect elongated test objects such as pipes, rods and bars, and more particularly to a phased array NDT/NDI system that rotates phased-array inspection probes around these test objects which are fed into the inspection system in a longitudinal direction during the inspection.

BACKGROUND OF THE INVENTION

The test and examination of objects such as fabricated structures and processed materials, without damaging them, is now of immense importance in a wide range of industrial situations. The benefits obtained by inspecting the physical condition of an object to ensure that it meets its specifications are well known to manufacturers. Perhaps, most notable among these benefits are the improved efficiency and product quality gained by preventing the use of non-conforming material in a manufacturing process. Cylindrical structures, such as pipes and rods, and non-cylindrical materials, such as cast bars, comprise a large population of these objects.

Perhaps the most widely used NDT/NDI material inspection methodologies today utilize ultrasound (UT) and eddy current (EC) probes, both of which include single element and/or array probes. They are used to detect and characterize static defects or anomalies in metal, non-metal, or fiber composite structures in conjunction with rapid manufacturing processes.

One of the most difficult challenges encountered when inspecting these materials arises from the fact that the orientation of defects is typically unknown prior to inspection. Accordingly, conventional inspection probe systems are capable of scanning the test object at a plurality of incident inspection angles—such as, longitudinal, transverse, normal and oblique. This requirement for complex multi-angle inspection places a significant burden on system design, manufacturing, and maintenance.

The present disclosure is primarily concerned with two types of NDT/NDI systems that are commonly referred to as 'pipe' (or test object) and 'bar' inspection systems, such as the ones provided by the assignee of the present disclosure, i.e., the Olympus-NDT company. Furthermore, the present disclosure primarily describes exemplary inspection methodologies that employ phased-array or single element UT probes; however, it is not limited in this regard. Indeed, inspection methodologies that employ eddy current, acoustic, and other probe sensor technologies may also benefit from the teachings of the present disclosure.

The test objects for which these systems are used can be very long, e.g. 15 meters, with a wide range of diameters or cross sectional dimensions. For example, conventional pipe inspection systems can cover a range of diameters from 60 to 620 mm and wall thicknesses ranging from 4 to 50 mm. Conventional solid bar inspection systems can cover a range of diameters from 8 to 250 mm. Accordingly, the industrial setting where these products are produced and inspected must provide substantial material handling capabilities, factory floor space and other equipment resources.

Conventional pipe inspection systems (PIS) usually comprise:
a) a transport mechanism to feed or place the test object to be inspected in the proper test location;
b) a plurality of phased-array test probe heads positioned along the test object's longitudinal axis for the purpose of sensor data acquisition at multiple incident angles, which probe heads are operable to be moved axially and coupled along said axis while the test object is rotated in an axially stationary position;
c) a couplant irrigation system to provide an ultrasonic coupling medium, such as water, in a laminar fashion interposed between the surface of the probe heads and the test object;
d) a means to correlate the inspection sensor data acquired with the location on the test object where the inspection measurement was made; and
e) a computerized system for motion control and data acquisition.

A conventional bar inspection system (BIS) is comprised of most of the same elements of the PIS described above; however, they differ with respect to element "b" in that the 'plurality of test probe heads' are instead disposed in a stationary manner to surround and be coupled to the perimeter of the test object while the test object is transported axially. Typically, two or more parallel plane probe head arrangements (cartridges) are used to provide maximum perimeter inspection coverage, each with a circumferential offset to cover the zone that the others do not.

It should be noted that the specific method utilized to supply the coupling medium, such as water, between the probe head and the surface to be inspected varies from system to system, such as UT, PIS and BIS. Specifically, a PIS employs a continuous local stream of water with laminar flow for each probe head, whereas a BIS employs a large tank of water in which the probe heads and the region of the test object to be inspected are submerged together. Furthermore, an entry and exit hole is placed on the opposing sides of the tank for the test object to be axially transported therein. As expected, considerable challenges are posed by the need to seal the interface between the tank holes and the moving test object in order to minimize water leakage and maintain adequate water volume.

The water tank method is used instead of the probe head longitudinal axis transport method when the UT methodology is used in line with another stationary inspection methodology, such as EC inspection. In this case, the test object is axially transported through the closely positioned and stationary UT and EC inspection systems, spending a portion of the test cycle time in both. Accordingly, this presents a practical limitation on axial movement of inspection probe heads.

Notable drawbacks associated with the conventional PIS can be attributed to the following characteristics of PIS systems.
a) Substantial and precise motion control requirements are placed on the system mechanics due to the need to transport and rotate large and heavy test objects, and transport major portions of the test system as well. These requirements demand a high initial investment, increased maintenance costs, greater design and assembly complexity, produce occasional performance anomalies (such as encoder slippage), large power consumption, and overall equipment wear and tear. There are also production delays associated to loading the test object on the inspection conveyor.

b) Adequate inspection coverage of the test object surface requires probe sensors operable to produce a plurality of incident inspection angles to deal with the fact that a flaw, such as a crack, may be orientated in the blind spot of a particular probe.

Accordingly, provisions must be made to ensure that each point on the outer surface of the inspected object is capable of being coupled to either: i) one probe with the ability to operate dynamically with multiple incident angles and/or apertures and/or ii) a large plurality of probes disposed in such a way as to achieve the same end.

The drawback associated with expedient 'i' above is that the motion of the test object has to stop, or be substantially slowed, to ensure that the probe couples the programmed range of incident angles at each point required on the inspected surface. Furthermore, the pulse repetition frequency (PRF) and speed of the data acquisition system needs to be quite high to ensure that the inspection throughput is not further compromised. Conversely, the inspection throughput can be increased, but only at the expense of reduced of inspection coverage, which results in lower inspection quality.

The drawback associated with expedient 'ii' above as compared to expedient 'i' above is primarily due to a large number of probes needed which require considerably more space due to the need for additional motion control apparatus and data acquisition units (DAU's). Furthermore, effecting motion control of the probes and the DAU's electronic enclosures is quite complex, including the need for cable management of probes, power, and external communications.

The most significant drawbacks associated with a conventional BIS are the same as those described above for the PIS, except that the test object is typically not rotated during inspection and the problems described above associated with the use of a water coupling tank are present.

Attempts to overcome the aforementioned drawbacks are exemplified by the teachings of U.S. Pat. No. 7,293,461 (Girndt) and U.S. Pat. No. 5,007,291 (Walters et al), both of which are summarized as follows.

Girndt teaches a method for ultrasonic inspection of tubular objects with a fixed set of parallel stationary circular arrays of composite transducers disposed and oriented to achieve thorough inspection coverage for the detection of anomalies, such as transverse, wall or longitudinal defects. To this end, Girndt employs composite transducers, which provide inspection area coverage greater than achievable with the same number of conventional non-composite transducers. Because many more non-composite transducers are required to cover the same area, the use of Girndt's arrangement of composite transducers reduces the number of channels needed for inspection of the tubular. More specifically, the primary advantages of composite transducer piezoelectric crystal material as compared to the conventional non-composite variety are: a) its face can be formed into a cylindrical or spherical shape that allows the UT beam to be focused without the need for an additional lens in front of the crystal face, and b) it provides a much higher excitation acoustic pulse for a given drive voltage which significantly improves the signal to noise ratio of the received echo.

The most significant drawbacks of Girndt's method involve a large number of transducers required for good inspection coverage as compared to a rotating probe system described below, and the difficulty to adapt to a wide range of test object diameters and wall thicknesses using a fixed set of composite transducers. As one might expect, a large number of transducers substantially increases system cost and complexity due to the number of DAU channels for signal processing. Furthermore, considerable changeover time is required to adapt Girndt's inspection system from one type of tubular geometry to another, which is beyond the inspection capabilities of a given set of composite transducers. Production system down time results in considerable productivity loss for the test object manufacturer. Furthermore, the test object manufacturer must invest in a separate set of curved face transducers for each test object size they produce that cannot be tested with the first set.

Walters et al. (U.S. Pat. No. 5,007,291) teaches a method for ultrasonic inspection of pipes that overcomes several aspects of the aforementioned background arts. The disclosure's use of multiple pairs of transducers (i.e. probes) disposed in linear, axial array for transmitting in each of the longitudinal and plurality of oblique directions increases the scan coverage for each revolution of transducers and therefore reduces the time required for an inspection.

In order to overcome the drawbacks associated with connecting a large number of transducer signals between the rotating and stationary parts of the inspection system, Walters teaches summing the response signals from all transducers in a "bank", prior to providing them in analog form via a slip ring connection to a stationary amplifier module. Walters employs a plurality of transducer banks, each set to a fixed inspection incident angle. The transducers within each bank are mounted at a fixed angle to couple the UT pulse with the test object surface at one of a longitudinal, transverse, normal or oblique angle. In some cases, the transducers contained in the banks are complementarily oriented to face in either the forward or reverse clockwise rotational direction to maximize inspection coverage.

Although Walters' teachings overcome many of the aforementioned drawbacks of the background art, it falls short of providing easily and dynamically set, and wide variety of incident inspection angles and focal depths of the probe banks. In addition, as can be readily appreciated by those skilled in the art, the use of a slip ring connection for analog transducer signals poses problems associated with signal noise, limited bandwidth and a limited number of signal connections.

A review of the prior art can therefore be summarized that conventional ultrasound inspection systems as well as phased-array test object rotating inspection systems both have limitations in terms of the quality of the inspection, productivity, and cost effectiveness.

As phased-array technology is the current state of the art inspection method for performing full range inspection of test objects, it would therefore be beneficial to apply this technology to rotating head inspection systems thereby taking the advantages of providing inspections with higher resolution and higher through-put without the aforementioned disadvantages associated with conventional test object rotating system and rotating fixed incident angle probe inspection systems.

In view of the background art described above, a solution that more effectively addresses the noted drawbacks would be greatly appreciated by those in need of more efficient, reliable and cost effective inspection systems. The specific improvements required to accomplish this solution pertain to simplifying the motion control requirements for both the test object and inspection system, reducing the amount of floor space required for the system, allowing easy adaptation to a wide range of elongated test object sizes, and achieving optimal inspection performance by providing a means to allow a wide range of inspection probe incident angles and focal depths.

SUMMARY OF THE INVENTION

The invention disclosed herein aims to solve the problems related to cost, productivity and performance associated with phased-array inspection systems. More particularly, the present invention relates to a system intended to inspect test objects by rotating at least one phased array probe, obviating the need to rotate the test objects, which is particularly problematic when large objects are involved in inspection.

Accordingly, it is a general object of the present disclosure to provide a rotating phased-array inspection system employing one or more phased array rotating inspection heads moving in an encircling motion around the test object, when the test object is fed in longitudinal direction.

It is further an object of the present disclosure to make use of small and robust data acquisition units (DAUs), which can be installed directly on-board the rotating inspection head, in close proximity of the probes.

It is further an object of the present disclosure to make use of the advantages of wireless data transmission technology to transmit acquisition data from Data Acquisition Unit to an external dedicated application which is able to process the signal data, build the inspection displays, present the results and manage the alarm events in case of defects.

It is yet further another object of the present disclosure to enable inspections with the high precision and versatility provided by the phased-array technology, including wall thickness measurements and detection of longitudinal, transversal, oblique, and lamination defects by electronically scanning and steering of the acoustic beams.

It is yet further another object of the present disclosure to provide electricity, couplant fluid, and pressurized air to the rotating section of the rotating phased-array inspection system by means of a stationary source or local source on the rotating section.

These and other objects of the present disclosure can be realized with a test system for performing non-destructive testing of an elongated test object, wherein the test system includes: a test object conveyor for conveying the test object along a longitudinal conveyance path; a probe assembly including phased-array probes, the probe assembly being configured to induce signals in the test object and sense echoes reflected from the test object; a probe assembly conveyor configured to movably support the probe assembly, to move the probe assembly on a circumferential path about the test object; and a control system coupled to the test object conveyor and to the probe assembly conveyor and configured to allow data acquisition by and from the phased-array probes while, simultaneously, the test object moves along the longitudinal path and the phased-array probes move on the circumferential path. The test system may include phased-array probes of different types to optimize detecting faults or cracks in the test object which extend in different directions. Further, phased-array probes of a same type may be located so they are circumferentially juxtaposed to one another. The probe assembly conveyor may include a first, stationary bearing structure which rotatably supports a second, rotatable bearing structure, wherein the second bearing structure is configured to support the probe assembly.

BRIEF DESCRIPTION OF THE DRAWINGS

FIG. 8c is a diagram showing the interlaced helical scan pattern produced by the rotating phased-array inspection system using two eight aperture probes disposed 180 degrees apart.

FIGS. 9a and 9b are diagrams showing a perspective and plane view of an alternative embodiment employing a stationary couplant irrigation system.

FIG. 10 is a diagram showing an alternative embodiment with the use of multiple (two in the exemplary case) rotating PA probe assemblies along the longitudinal axis of an elongated test object and a transport mechanism used to reposition a rotating PA probe assembly in the axial direction of the test object.

DETAILED DESCRIPTION OF PREFERRED EMBODIMENTS OF THE INVENTION

It should be noted that terms such as "pipe(s)", "tube(s)", "bar(s)", etc., are exemplarily used as the "test object(s)", and therefore these terms are used interchangeably in the present disclosure. Further, "water" and "couplant", as well as "air" and "gas", are also herein used interchangeably.

Figure 1:
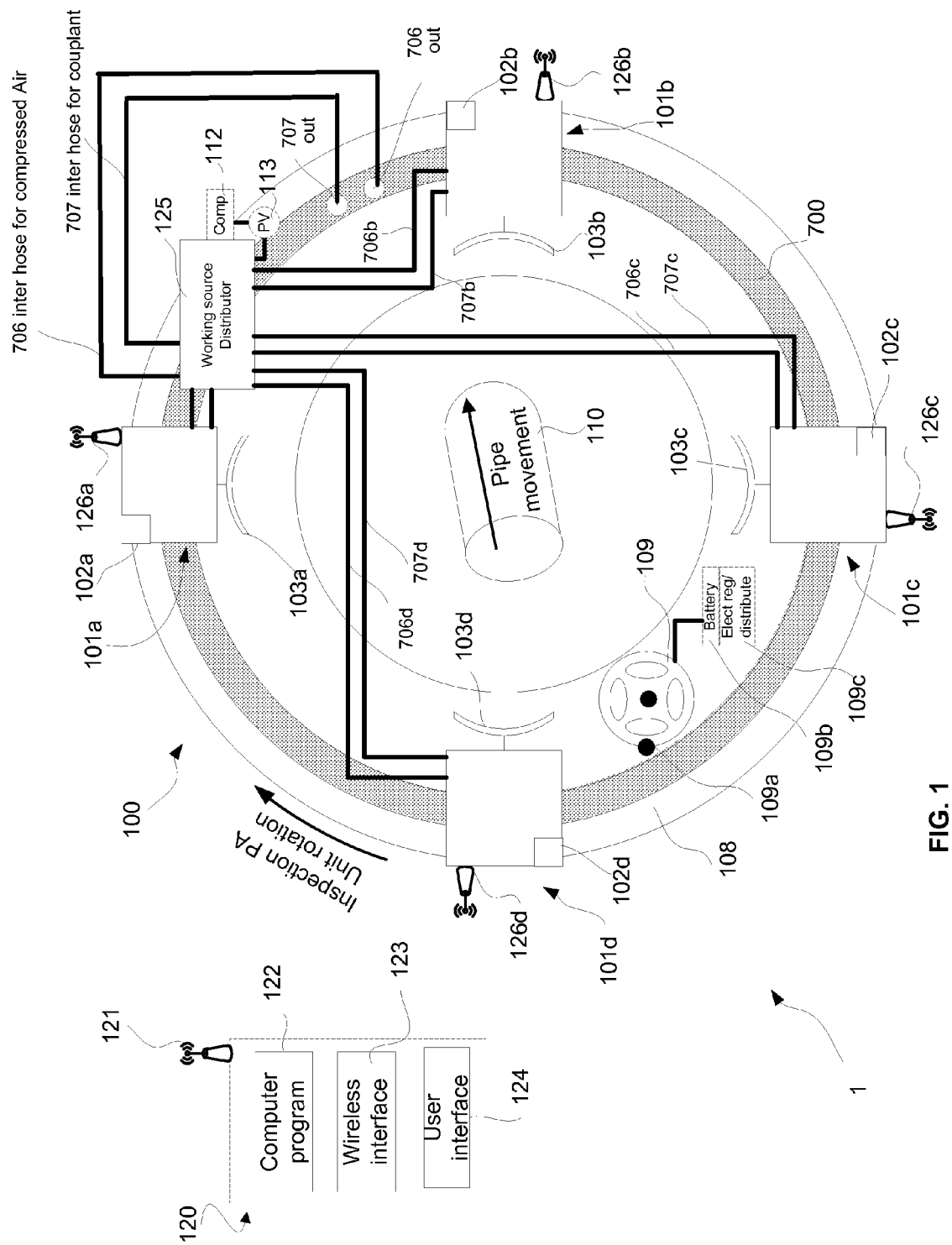
FIG. 1 is a schematic diagram showing the preferred embodiment of the presently disclosed rotating phased-array system, wherein optionally four PA probe head units are employed.
Figure 2:
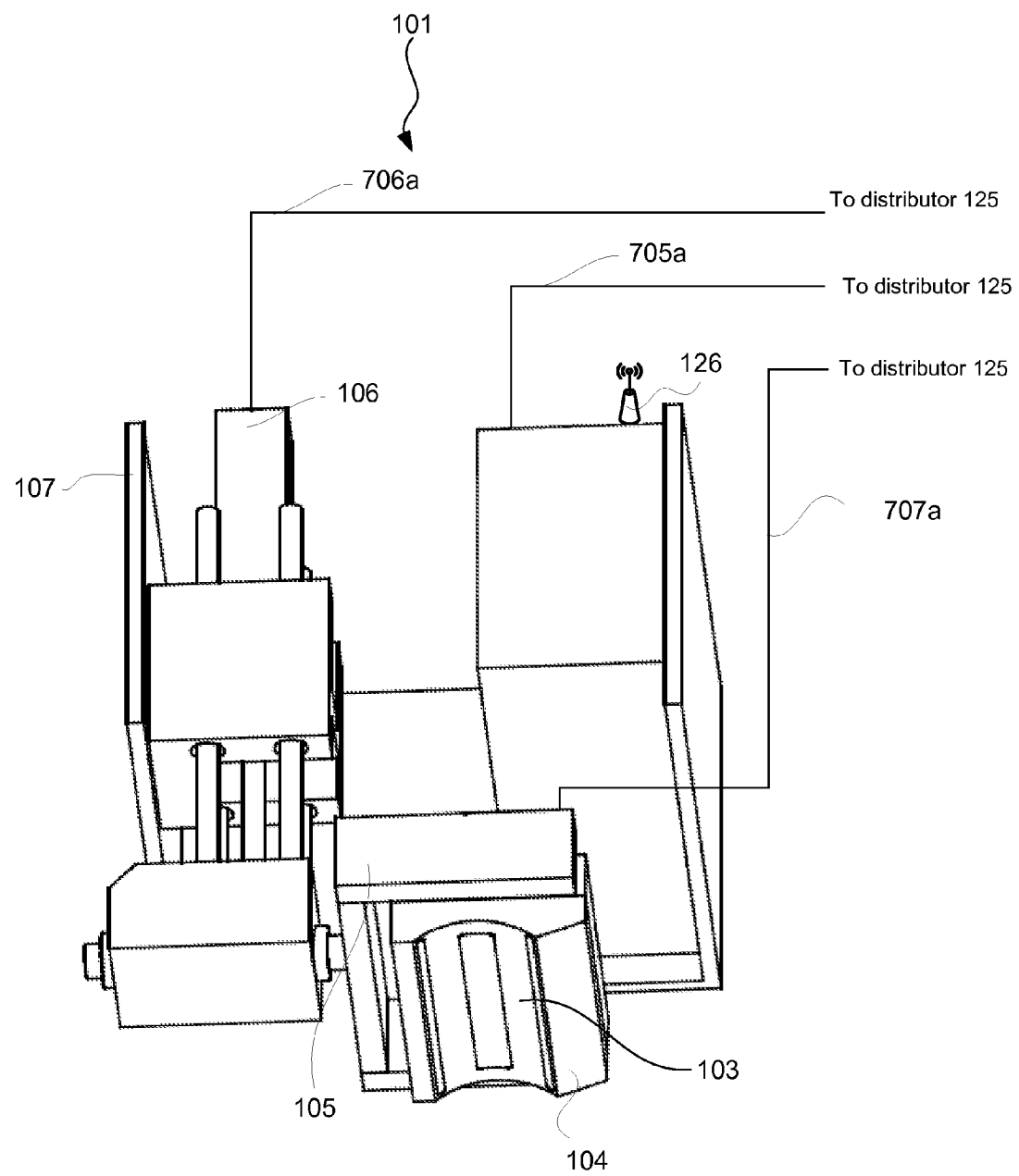
FIG. 2 is a diagram showing one of the four inspection probe head units, the elements of which can be applied to other inspection probe head units.

It should be further noted that when referring herein to figure item numbers, a numeral without a letter suffix is meant to denote all items in the figure that bear the same numeral with a letter suffix. For example, 'probe head unit' 101 shown in FIGS. 1 and 2a is meant to denote 'Probe head unit' 101a, 101b, 101c and 101d in FIG. 1. Furthermore, the item numbers used for PA probe head unit 101 shown in FIGS. 1 and 2 are not shown in 101b, 101c and 101d, but are implied.

It should be understood that the subject titles used in the subsequent description are for the purpose of making the description more organized and easier to be followed. However, the scope of any content of the description under any subject title should not be construed with any restriction, and the content of the description, regardless of any subject title should be construed in its entirety.

The Rotating PA Probe System

Referring to FIGS. 1, 2, 7a, 7b and 7c, the preferred embodiment of the presently disclosed rotating PA probe system is an apparatus comprised of:

a. conveyor 1004 (FIG. 10) for feeding a test object 110 lengthwise through a test inspection zone encircled by rotating probe head units 101;

b. at least one rotating probe assembly, which is further comprised of:

i. one or more inspection probe head unit 101 circumferentially disposed on a rotating plate 108, each probe head unit 101 includes one or more phased-array probes 103, which preferably are linear array probes mounted with probe's active axis parallel to the test object's longitudinal axis;

ii. a probe unit positioner 106 (in FIG. 2), preferably of the pneumatic type, operable to adaptively position the phased-array probes in relation to the test object surface in order to couple and decouple the probe sensors;

iii. a compressed air, probe couplant and electronic coupling ring 700 (FIGS. 1, 7a, 7b and 7c) and a working source distributor 125 to provide an ultrasonic coupling medium, such as water, to water wedge that is normally interposed between the surface of the probe head 103 and the test object, and to provide compressed air for operation of pneumatic cylinder, electric power source for probe operation;

iv. a data acquisition unit or units 102 mounted on rotating plate 108 operably connected to each probe head unit 101 for the purpose of acquiring and processing data from the probe sensors and communicating with user operating station 120 by means of a wireless transceiver 126;

v. a rotation drive 702 or 704 (FIG. 7) to rotate rotating plate 108 at a predetermined speed (RPM) on a bearing 703;

vi. a circumferential sensor 708 for determining the circumferential position of rotating plate 108 with respect to a known reference, such as the twelve o'clock position of zero degrees, and, c. a user operating station 120 comprising user interface 124, wireless interface 123, and a computer program 122 for alarm event detection, control/monitoring of rotating probe assembly 100 including operation of conveyer 1104, and data processing to correlate the acquired inspection data with the surface location on the test object where the inspection measurement was made.

Conveyor 1004 (FIG. 10) is comprised of at least two conveying members, one of which is an 'active' roller device, either 1004a or 1004c, that exerts a drive force on the test object to move it in the axial direction. Other optional conveying members, such as 1004b may be active roller device or a 'passive' roller device that provides only support and directional guidance to test object 110. Conveying members may be movable to adjust transport direction or be removed from the transport path.

Each of DAUs 102 in FIG. 1 collects inspection signals from corresponding PA probe 103 and transmits the data to computer program 122 via wireless connection 121. DAU 102 is preferably configured to be able to receive command from operating station 120 to further apply firing command to PA probe 103 according to predetermined focal laws. DAU 102 is also capable of acquiring inspection signals and producing A-scan data for a corresponding geometric location of test object 110. DAU 102 is also optionally configured to provide alarm signals based on predetermined threshold and/or gate. A desired level of on-board data processing conducted directly on DAU 102 provides the advantage of less demanding real time data transmission via wireless transceiver 126.

Wireless data interface 123 is provided to manage all of DAUs 102 and the operation of the rotating PA system 1 simultaneously.

It should also be noted that DAUs 102 may employ transmitters only with operation control information provided from operating station 120 to DAUs 102 by means of slip ring interface 705 described later in relation to with FIG. 7b &c.

The management of DAUs 102 involves providing them with the appropriate inspection parameters (such as probe incident coupling angles), collecting data from each DAU, rebuilding the inspection results for on-screen displays, and emitting alarm events in case of defect detection.

Referring now to FIG. 2, each of probe head unit 101 further comprises a probe holders 104, mounting yokes 105 install on pneumatic positioner 106 via mounting plate 107. Rotating plate 108 provides probe head unit 101a continuous and complete rotating movement from 0 to 360 degrees at a preferably constant speed.

Continuing with to FIG. 2, probe holder 104 is coupled to pneumatic positioner 106 by mounting yoke 105. The activation (opening) of pneumatic positioner 106 pushes probe holder 104 to couple to the test object surface, at the start of the inspection. Vice versa, the deactivation (closing) of pneumatic unit 106 retracts probe holder 104 from the test object surface, at the end of the inspection.

Probe holder 104 allows installation of PA probes 103 with accurate positioning with respect to the test object surface and test object length (probe height, probe angle). In the preferred embodiment, reliable contact of the probe holder 104 on the test object surface 110 is provided by carbides known to those skilled in the art. Probe holder 104 is designed with necessary wear protection, adapted for use in an industrial environment. Probe holder 104 is installed in mounting yoke 105 which provides the necessary degrees of freedom to adapt to irregularities of the test object during the inspection.

Continuing with FIG. 2, each probe head unit 101 includes a mechanism allowing pre-adjustment of probe holders 104 to a predetermined distance from the test object surface. Accordingly, the closing distance (distance between the sensing surface of PA probes 103 and the opposing surface of test object 110 at test object arrival) preferably remains constant for any test object diameter to inspect. Optionally, an additional degree of positional flexibility is provided by a spring effect applied when a pneumatic cylinder unit 106 is at the end of its displacement stroke. This flexibility allows rotating PA probe assembly to be used with non-cylindrical and off center test objects 110. Furthermore, an alternate radial probe positioner (not shown) may be used when the degree of flexibility provided by pneumatic positioner 106 is not sufficient. In some cases, the non-circumferential and off center variance of test object 110 will be monitored proactively in order to allow time for the probe displacement mechanism to move into the proper location for inspection measurement.

It should be appreciated that many existing practice and design for PA probe positioning and adjusting can be incorporated by the present invention for the purpose of engaging rotational PA head to test object, and the resulted embodiments are within the scope of the present invention.

As seen in FIG. 2, one end of couplant irrigation hose 707a is attached to PA probe 103. The other end of tube 707a is attached to the working source distributor 125 as shown in FIG. 1, which manages the couplant supply from stationary outlet 707out (FIG. 7b).

Existing practices such as using water wedges and applying substantially laminar flow of couplant in region between the outer surface of water wedge and the opposing surface of test object 110 are preferably employed for the present disclosure and the resulting embodiments are within the scope of the present invention.

Similarly as shown in FIG. 2, one end of compressed air hose 706a is attached to pneumatic positioner 106. The other end of hose 706a is attached to the working source distributor as shown in FIG. 1, which manages the air supply from stationary outlet 706out (FIG. 7b).

Each PA probe 103 and probe holder 104 can be chosen or positioned to fit for a specific inspection task which includes detection of longitudinal, transversal or oblique cracks, lamination defects, drilled holes (through holes), and wall thickness variation. For example, longitudinal defect detection can require installing PA probes 103 with an angle of typically 17 degrees between the PA passive direction on PA probe 103 and the test object surface. Transversal defect detection requires installing PA probes 103 parallel to the test object surface in both the active and passive directions while data acquisition unit 102 provides focal laws in order to create the desired angle for the acoustic beam. Oblique defect detection requires a combination of angular positioning of the PA probes 103 and steering the beam.

Figure 3A:
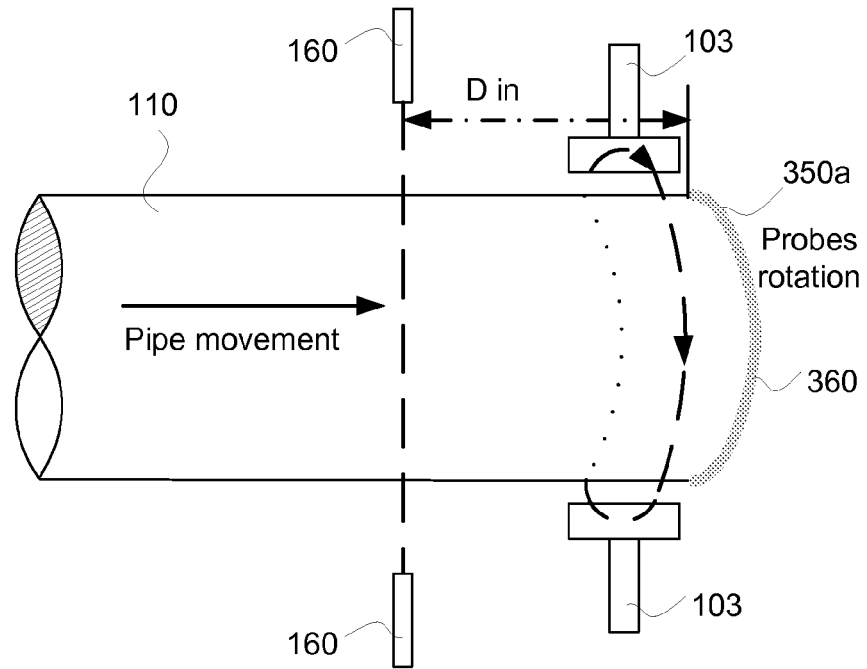
FIGS. 3a and 3b are diagrams showing the start and end position, respectively, of inspection of test object being passed though the rotating PA head units.

Reference is now made to FIG. 3a, in which the inspection starts with the exact positioning of the PA probes 103 on the test object's entering head (initial extremity) 350a. This positioning aims at providing a minimum distance between a sensing location of PA probe 103 and the initial test object axial extremity. This distance defines the dead zones 360 of the inspection and typically must be minimized.

The activation and deactivation of pneumatic cylinders 106 (FIG. 2) is controlled by at least one test object presence sensor 160 that detects the presence or absence of the moving test object 110 in the vicinity of PA probes 103. The exact moment to activate/deactivate the pneumatic cylinders takes into consideration the distance between object sensor 160 and PA probes 103, and the length of PA probes 103. At the head of the test object (350a in FIG. 3a) and at the end of the test object (350b in FIG. 3b), the distance between test object presence sensor 160 and PA probes may be slightly different (respectively Din and Dout), due to the length of the PA probes 103.

Figure 3B:
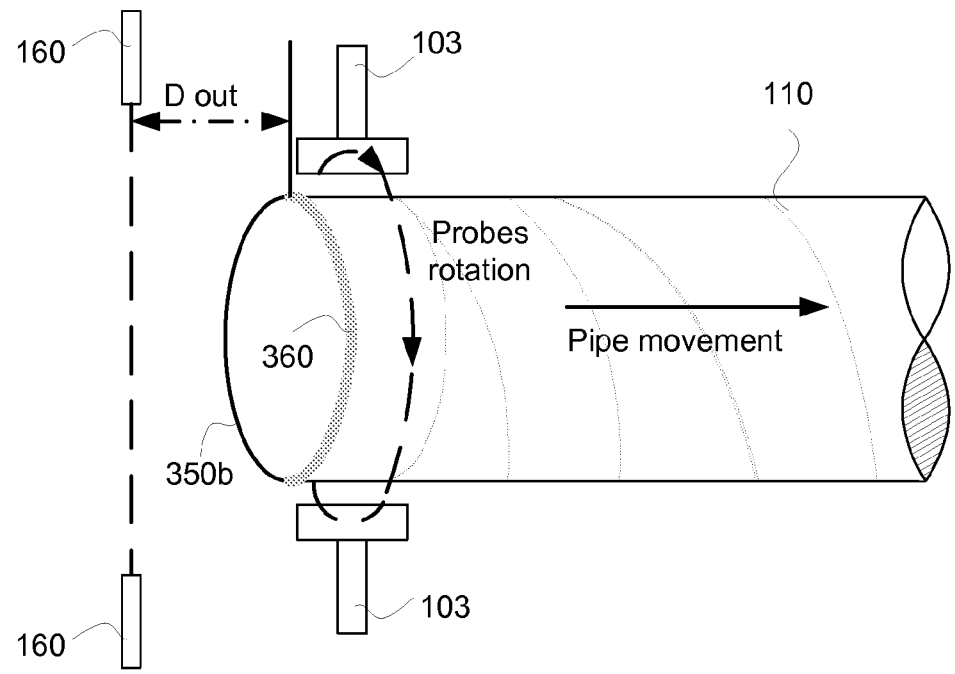

Continuing with FIGS. 3a and 3b, in order to have 100% of the length of the test object inspected, except for dead zones 360 at both axial extremities, the following operation procedure is employed due to width of the PA beam. A typical dead zone for any test object inspection probe assembly can be around 5 or 10 mm for most of the defect types. Due to the rotational movement of PA probe head units 101 and linear translation of test object 110, PA probes 103 follow a helical path around test object 110. At the head and at the end of the test object, the PA probes 103 are continually rotating when the test object is stopped to minimize the dead zone at each axial extremity.

The rotation speed of rotating plate 108, axial traveling speed of test object 110 and the coverage of PA probes 103 are partially defined as a function of the maximum pulse repeating frequency and acquisition rate of a specific setup of PA probe 103 and DAUs 102. The maximum linear and rotation speeds are calculated and set by dedicated computer program 122, thereby ensuring the inspection of the whole length of test object 110 except for dead zones 360 at the extremities of test object 110.

Inspection Procedure Using the Presently Disclosed Rotating PA System

Figure 4:
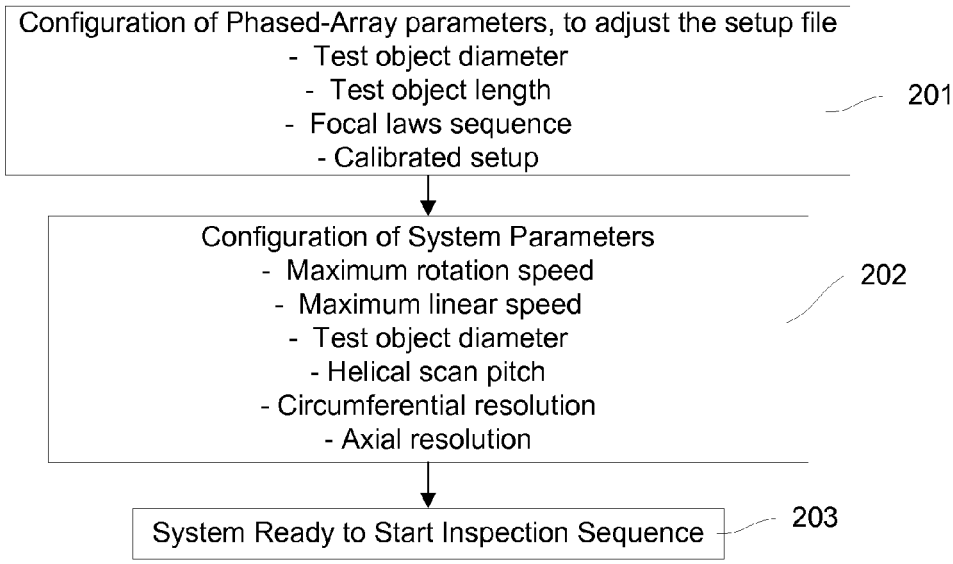
FIG. 4 is a flow chart diagram showing the typical operation steps before starting the test object inspection using the presently disclosed rotating PA inspection system

Reference is now made to FIG. 4, which shows the inspection set-up process for a phased-array rotating head inspection system 1 according to the present disclosure. In step 201, system 1 adjusts the "phased array probe parameters" for the inspection session according to the initial values provided for the specific inspection session. The initial values could be from a combination of sources, such as operator input and/or automatic probe recognition. The initial value also includes the setting of test object diameter, length, alarm gates, focal law sequences for the firing order and focal law delays, and calibration for homogeneous and coherent signals for all the focal laws. These parameters are sent to Data Acquisition Units 102 via dedicated computer program 122. In step 202, system 1 establishes "system parameters". The main system parameters include the maximum rotation speed, maximum linear speed, test object diameter, helical scan pitch, circumferential resolution and axial resolution. System parameters are calculated prior to inspection sessions according to Eqs. 1, 2 and 3, which are described later in this disclosure. Once all of these parameters are set up, system 1 is ready to start the inspection sequence in step 203.

Figure 5:
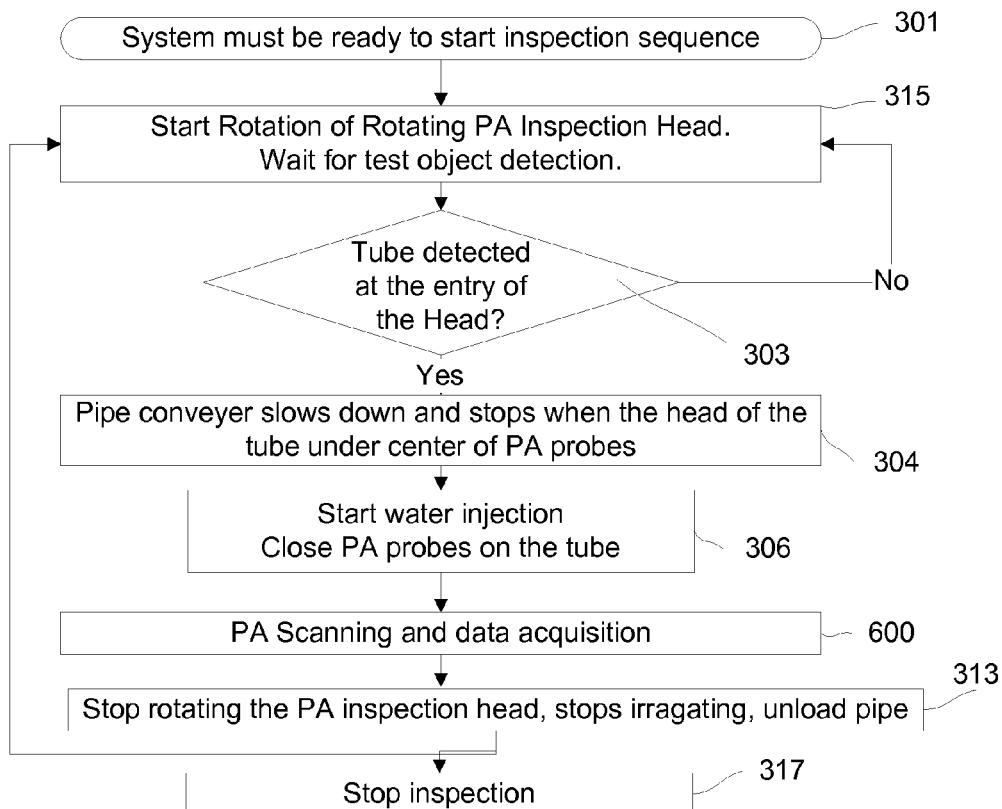
FIG. 5 is a flow-chart diagram showing operational steps used in performing an inspection using the presently disclosed rotating PA inspection system.

Moving to FIG. 5, the inspection sequence for test object inspection using rotating PA probe system 1 is now described. The inspection starts with step 301, loading a previously configured setup in dedicated computer program 122 with the information mentioned in 201 and 202. In step 315, rotating plate 108 starts rotating in order to reach the necessary rotation speed for the inspection. In step 303, once the target rotation speed is reached and the test object 110 is detected by sensor 160 to be entering rotating PA assembly 100, test object 110 is axially slowed down in step 304 and stopped when the head of the test object (350 in FIG. 3a) is under PA probes 103. In step 306, couplant irrigation supplied from $707_{out}$ in FIGS. 1, 7b and 7c, (alternatively 900 in FIGS. 9a and b) is applied in preparation for and during the activation of PA probes 103 onto the test object surface. At this time, the system is ready to start acquiring inspection data in a scanning and data acquisition step 600, which is detailed in FIG. 6.

Figure 6:
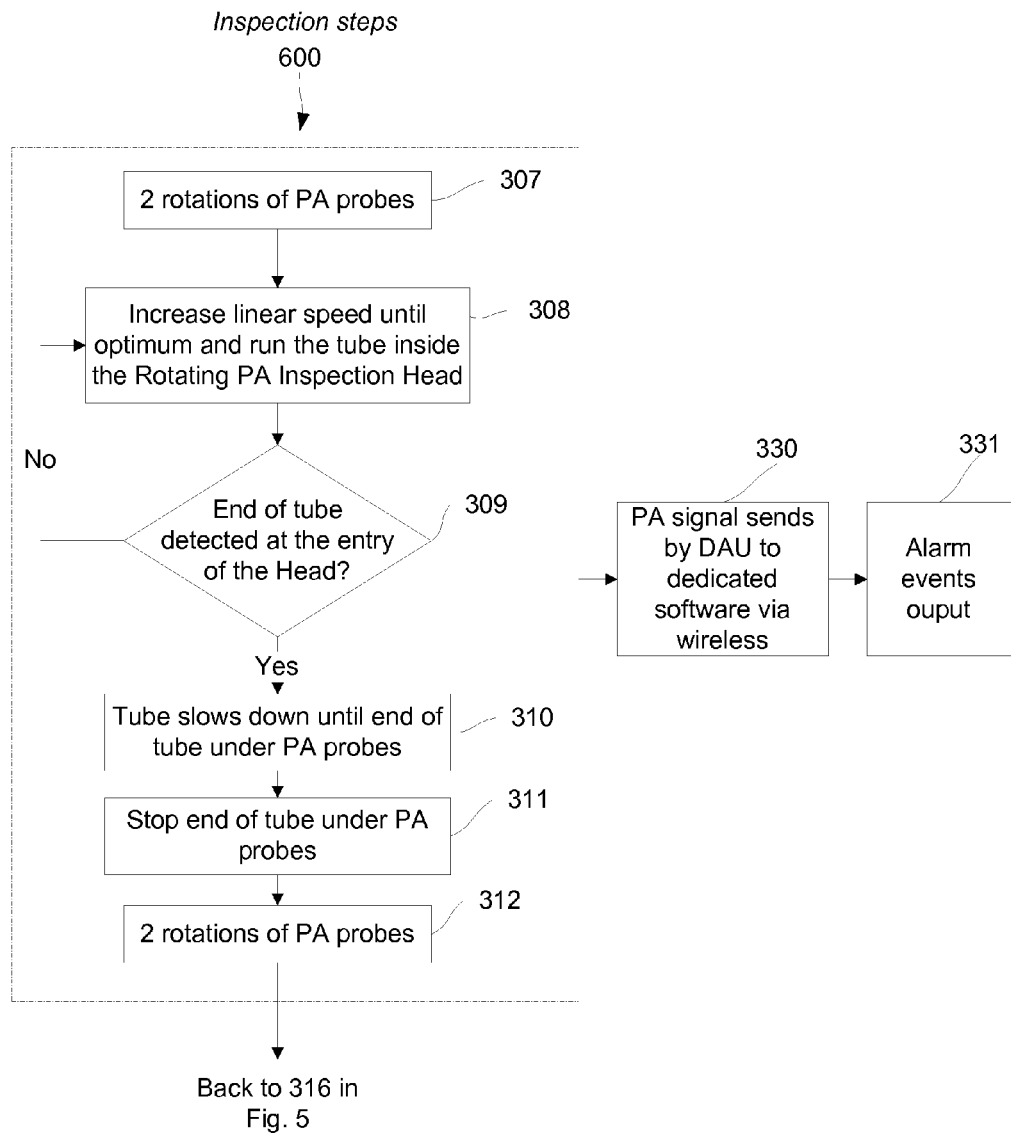
FIG. 6 is a flow-chart diagram showing detailed scanning process during an inspection using the presently disclosed rotating PA inspection system.

In FIG. 6, the scanning of the test object typically starts with at least one or two complete rotations of probe head units 101 without linear movement of the test object in order to completely inspect the head of the test object (step 307). Then in step 308, the linear speed of the test object is increased until reaching the nominal speed. In step 309, the test object then is translated until its end, detected by object presence sensor 160. At this time, the test object slows down (step 310) and is stopped with the end of test object under PA probes 103 (step 311). Typically at least one or two complete rotations of probe units 101 is performed without linear movement of the test object in order to completely inspect the end of the test object (step 312). PA probes 103 are then deactivated and water irrigation is typically stopped at step 313 back in FIG. 5.

During the scanning procedure described in step 600 (from step 307 to step 312), PA probes 103 are pulsing and receiving and DAUs 102 are acquiring inspection signals. DAUs 102 transmit data to dedicated computer program 122 via wireless coupling 121 and 126 (step 330). In the case of defect detection, an alarm is typically created in real time by DAUs 102 or by dedicated computer program 122 depending on the chosen alarm configuration (step 331).

Referring back to FIG. 5, at this time the inspection of the test object is complete and the test object is removed from rotating PA head inspection system 1 (step 313) by the test object conveyor 1004. Rotating PA inspection system 1 is ready to stop are start the inspection of the next test object (step 317).

It should be appreciated that it is within the scope of present disclosure that rotating PA head units alternatively may never stop rotating, while conveyor loads, transfers and unloads pipes 110. Object presence sensor 160 records and detects each of the starting and ending of each pipe, and the rotating PA system 1 continuously scans and records data corresponding to each pipe. It should also be noted that the object sensing function may be integrated within the PA inspection function.

Couplant, Compress Air and Electric Coupling Ring

Another important novel aspect of the present disclosure is the employment of working resource coupling ring 700 (in FIGS. 1 and 7a, b, c) that couples a stationary supply of pressurized air, couplant fluid, and electricity to probe units 101 located on rotating plate 108.

Figure 7A:
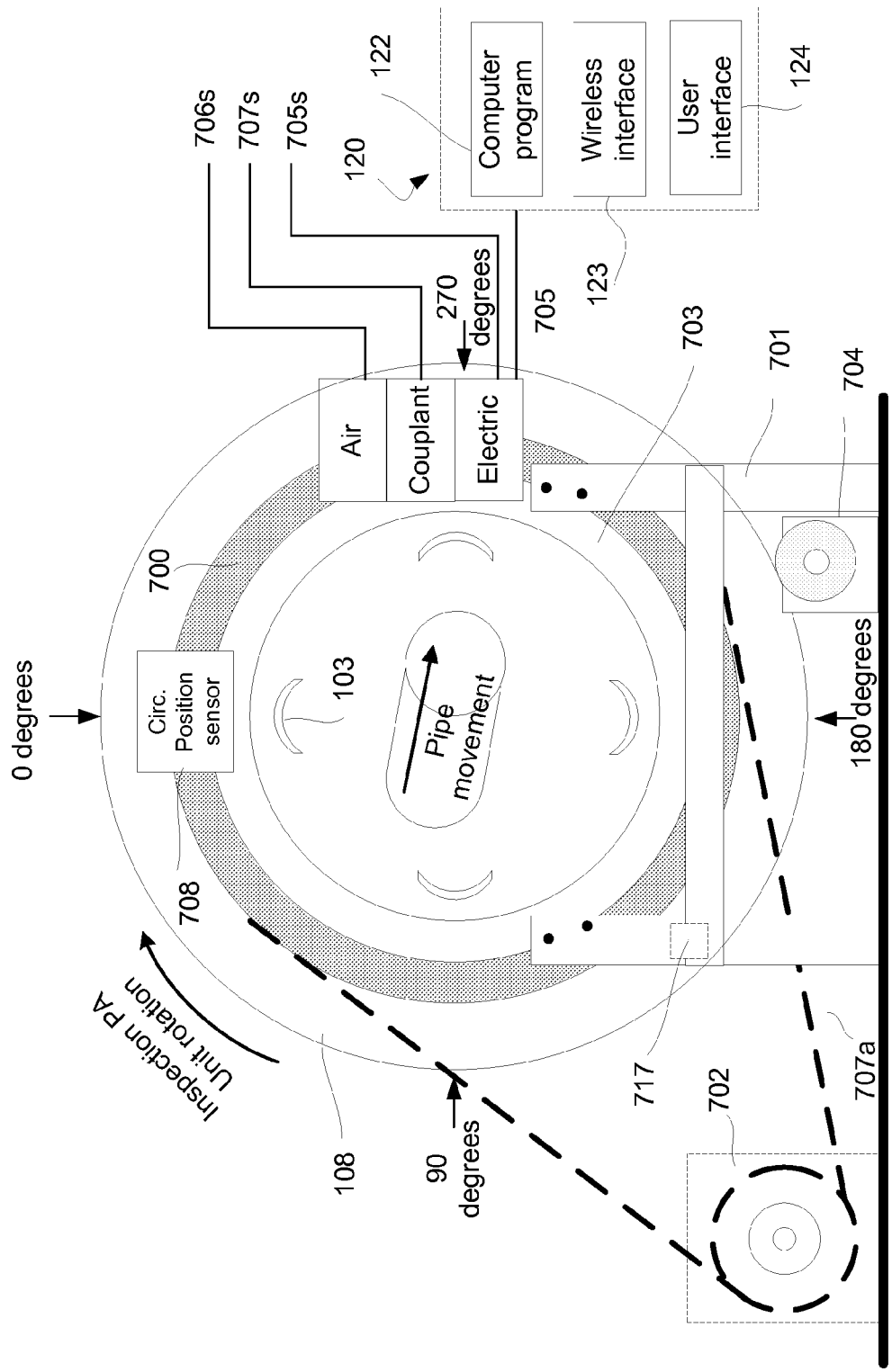
FIG. 7a is a schematic diagram showing the rotational drive assembly and the rotating coupling ring providing electrical, couplant and air supplies to the probe head units.

Referring now to FIG. 7a, rotating plate 108 is affixed to a bearing 703 that is mounted on support frame 701 and rotationally propelled by direct drive 704 or, alternately, by belt drive 702. The circumferential position of rotating plate 108 is determined by a circumferential sensor 708 that is preferably an optical encoder.

Also shown in FIGS. 1, 7a, 7b and 7c are pressurized air, or other suitable gas supply 706s and air supply interface 706, pressurized couplant supply 707s and couplant supply interface 707, and electrical/signal supplies 705s and slip ring interface 705. Pressurized air supply 706s is provided for the operation of pneumatic cylinders 106. Pressurized couplant supply 707s provides couplant to irrigate probes 103. Electrical/electronic connections 705s provide power and other electrical connections to rotating plate 108.

As previously mentioned in FIG. 1, an air supply, probe couplant and electronic coupling ring 700 are employed to transfer stationary supplies of compressed air 706s, probe couplant 707s and electronic working source 705s to rotating probe head unit 101. Coupling ring 700 can be optionally attached to bearing 703 or built as an integral part of bearing 703.

Figure 7B:
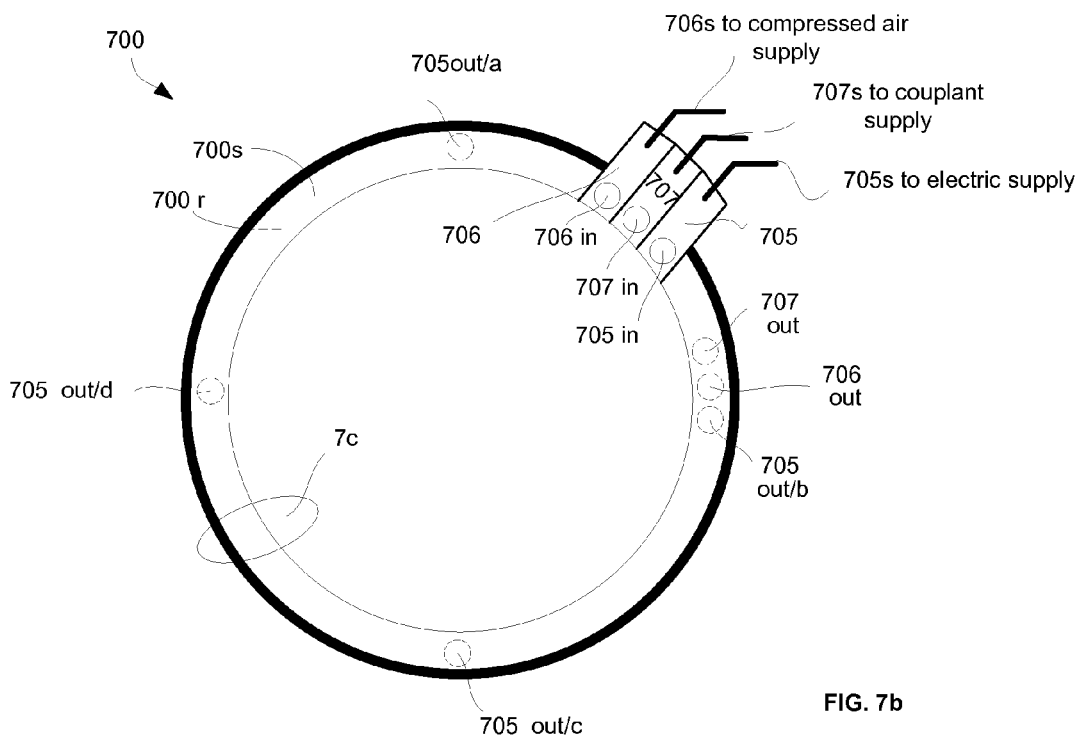
FIG. 7b is an elevation view of the coupling ring which is on one side (front) mounted to a stationary frame and on the other side (back) mounted to the rotating plate of the rotating phased-array inspection system.
Figure 7C:
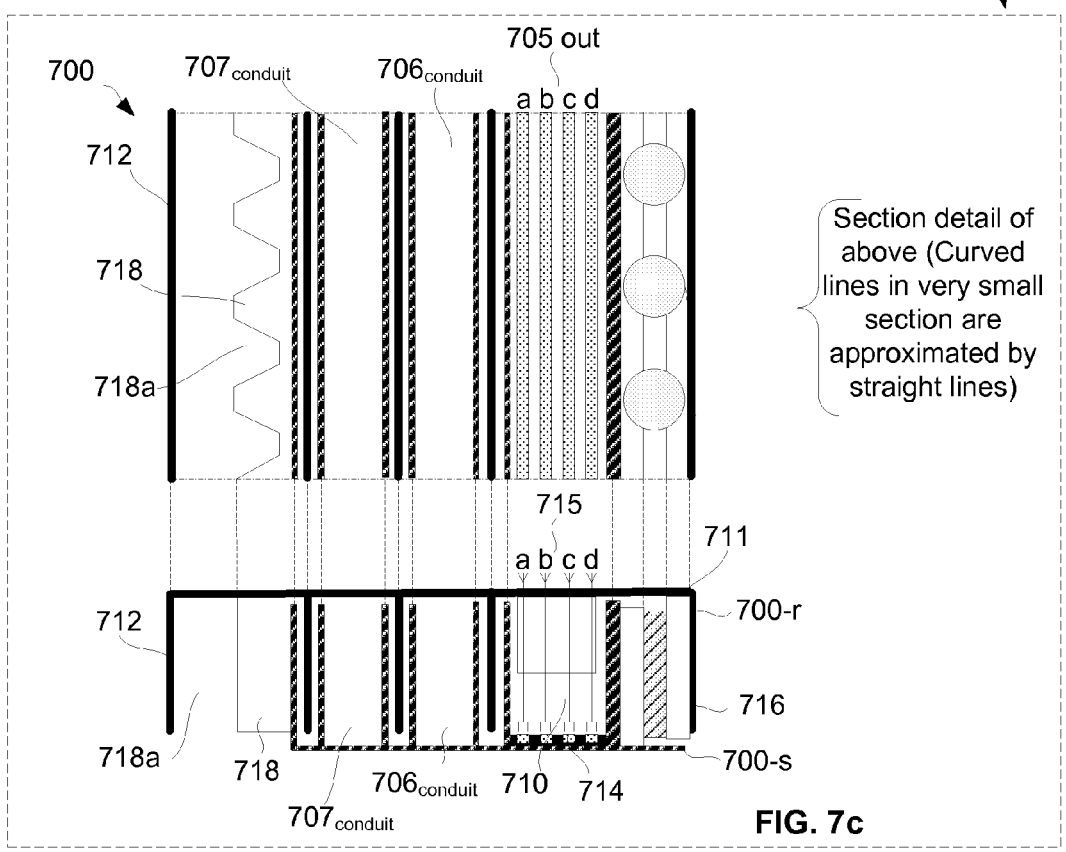
FIG. 7c is a cross-sectional and enlarged detail view of a small section inside of the coupling ring shown in FIG. 7b, showing the supplying channels for air, couplant and wiring.

Referring now to FIGS. 7b and 7c, coupling ring 700 is further comprised of a hollow circular chamber compartmentalized into a plurality of conduits, each of which is self-enclosed and sealed to house a specific kind of working source, either of compressed air, couplant, or electric power or signal. Coupling ring 700 has a stationary part 700-s, shown as the top part of 700 in FIG. 7b, which is affixed to bearing 703, which is further attached to support frame 701 (FIG. 7a). Coupling ring 700 further includes a rotational part 700-r, which is free to rotate, and shown as the back part of 700 in FIG. 7b.

Pressurized air supply is provided to air interface 706, the output of which is provided to intake hole $706_{in}$ of stationary part 700-s. Air intake hole $706_{in}$ is aligned with circumferential air conduit $706_{conduit}$ (FIG. 7c) within coupling ring 700, in which the pressurized air is provided for pneumatic cylinders 106 on rotating plate 108 through respective output hole 706out on rotational part 700-r.

Similarly, couplant supply 707s is provided to couplant interface 707, the output of which is provided to intake hole $707_{in}$ of stationary part 700-s. Couplant intake hole $707_{in}$ is aligned with circumferential couplant conduit $707_{conduit}$ within coupling ring 700. Liquid couplant is supplied to PA probe head unit 101 on rotating plate 108 through output hole 707out on rotational part 700-r.

It should be noted that seals or gaskets, not shown, are disposed between the stationary and rotating opposing circumferential walls associated with air conduit $706_{conduit}$ and couplant conduit $707_{conduit}$. The seals are used to maintain the pressurized air and couplant within their respective conduits.

The compressed air on the rotational conduit 700r is then further transferred via 706out to working source distributor 125 (shown in FIG. 1), and further distributed to each respective probe head unit 101 via hoses 706a, b, c and d shown in FIG. 1. Similarly, the couplant on the rotational 700r are then further transferred via 707out to working source distributor 125 (shown in FIG. 1), and further distributed to each respective probe head unit 101 via hoses 707a, b, c and d shown in FIG. 1.

Continuing with FIGS. 7b and 7c, slip ring cavity 710 of FIG. 7c also optionally includes circumferentially disposed conductors 714a-d on stationary part 700-s and respective spring loaded conductive contacts 715a-d on rotating part 700-r. Wires are respectively attached to the terminals of spring loaded contacts 715a-d for connection to devices on rotating plate 108 in FIG. 1. Electrical connections 705s are attached to the terminals provided for stationary conductors 714a-d in slip ring interface 705.

It should be noted that slip ring conductors 714a-d and 715a-d may be located instead on rotating part 700-r and stationary part 700-s respectively to achieve the same purpose. It should be noted that although not shown, slip ring conductors 715a-d are connected to probe head units 101 preferably by means of cabling provided by working source distributor 125, or alternatively may be connected at separate locations on rotating part 700-r that are in close proximity to probe head units 101.

Scan Resolution and Production Throughput Speed

Figure 8A:
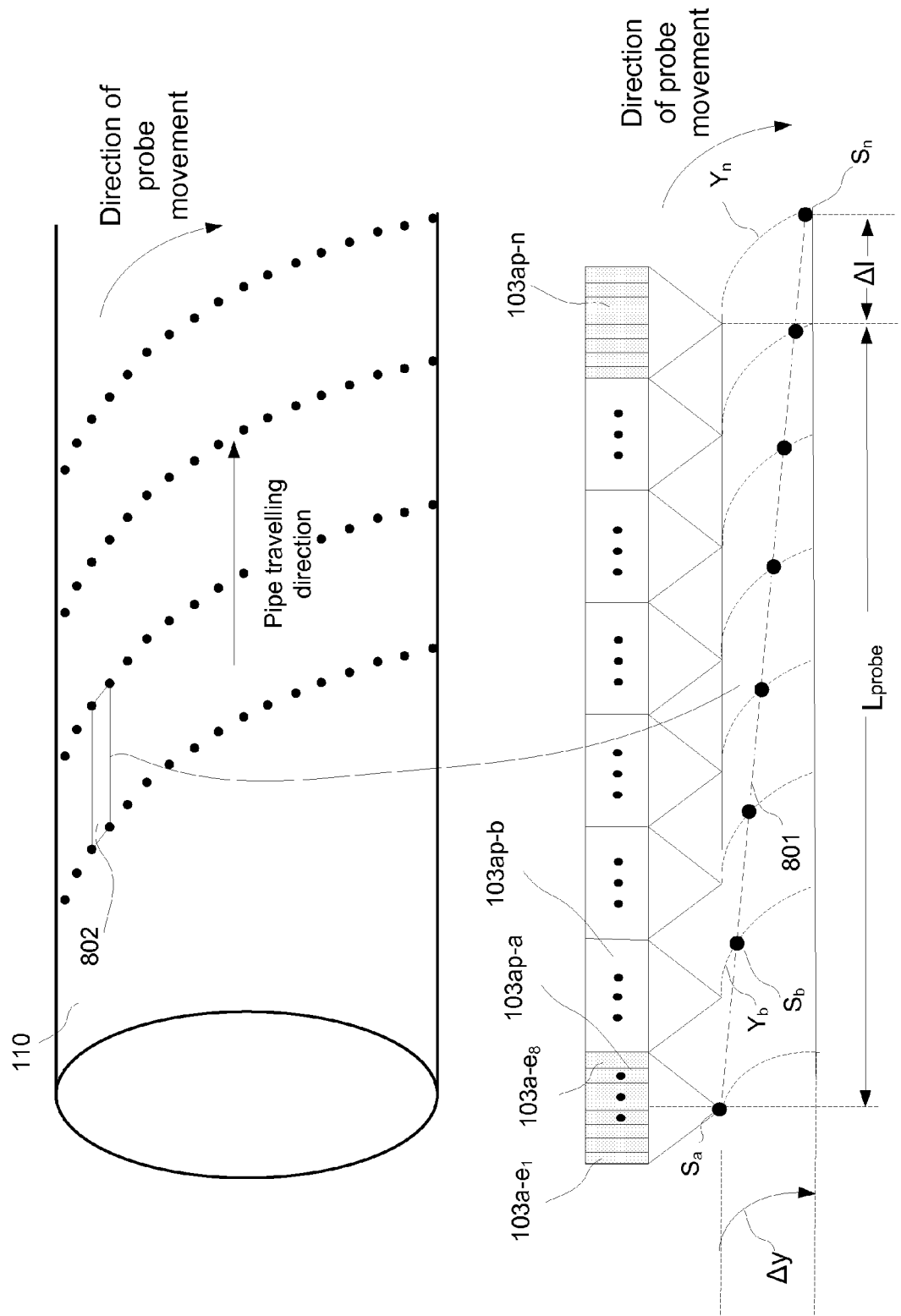
FIG. 8a is a diagram showing how the PA beams are fired from PA probe apertures of a PA head unit covering the test object contour.

Referring to FIG. 8a, a unit scan-area 802 delimited by a unit circumferential traveling distance Δy and a unit axial distance ($L_{probe}$+Δl) is enlarged and analyzed.

As shown in FIG. 8a, an exemplary phased array probe 103 has a total number of n apertures from 103ap-a to 103ap-n. Each aperture typically has k number of elements. For example, a "16/128" phased array probe will have eight 16 element apertures making up the 128 total elements. As shown in FIG. 8a, each aperture has 8 element, $103a\text{-}e_1, \ldots, 103a\text{-}e_8$, that is to say k=8 in this exemplary case.

Focal point of aperture 103ap-a, $S_a$, undergoes a pulse-receive measurement cycle when the 8 elements in aperture 103ap-a are applied a predetermined focal law. A complete linear scan is performed by successively applying focalized measurement cycles to aperture focal points $S_a$ through $S_n$ during scan cycle period Δt. Unit pipe contour travelling distance 801 shown in unit scan-area 802 is comprised of the measurements performed by each aperture ($S_a$ through $S_n$) while PA probe 103 rotates a circumferential distance Δy. The axial movement of test object 110 during one linear scan cycle (Δt) is Δl.

The following description explains how to provide 100% full area scan, and how to adjust scan resolution. Referring to FIG. 8a, the definition of relevant parameters is as follows.

a) $L_{probe}$ is the PA probe aperture span—i.e. the distance between the given element position in first aperture 103ap-a and the respective element position in the last aperture 103ap-n.

b) Δt, the scan cycle time, begins at the start of the pulse-receive cycle for aperture 103ap-a and ends at the completion of the pulse-receive cycle for aperture 103ap-n. $\Delta t^{-1}$ is the probe's "pulse repetition frequency".

c) $V_{pipe}$ is the speed that pipe 110 is fed (travels axially).

d) Δl is the axial distance that the pipe travels during Δt.
e) rpm is the rotating speed of the rotating plate 108.
f) T is the time it takes for the probe to rotate 360 degrees around pipe 110, which is rpm$^{-1}$.
g) $V_{aperture}$ is the speed of the PA probe head of each aperture scan cycle.
h) $V_{rotate}$ is the angular speed of the rotating plate 108.
i) n is the number of apertures of each PA probe 103.
j) m is the total number of probes of the rotating plate 108.
k) Δy is the unit circumferential scan resolution.

In order to make sure that 100% of the pipe area is scanned, the following Eq. 1 has to be observed. It should be noted that the scan resolution is finite, meaning that it produces surface measurements spaced at a fixed pitch when axial velocity, $V_{pipe}$, and rotational speed, $V_{rotate}$, are constant.

$$Vpipe \leq m \cdot Lprobe/T = m \cdot Lprobe \cdot (rpm)/60 \text{ (m/s)} \qquad \text{Eq. 1}$$

That is to say, the production speed is largely determined by the number of probes m and/or their rotating speed rpm.

When there is only one probe, the pipe traveling speed has to be one probe width $L_{probe}$ during one rotating cycle T in order to provide 100% of scan coverage. If the pipe is axially fed faster than one probe width during one rotating cycle T, there will be an un-scanned helical gap left behind the scanned area.

The circumferential scanning resolution, represented by the unit circumferential distance, Δy can be determined by Eq. 2:

$$\Delta y = Vaperture \cdot \Delta t/n = 2\pi R \cdot rpm \cdot \Delta t/n \qquad \text{Eq. 2}$$

That is to say, for a given linear scan speed, $V_{aperture}$, the circumferential scanning resolution is determined by the rotation speed (rpm). The higher the speed, the lesser the resolution (Δy). In order to maintain the circumferential scanning resolution at higher speeds for a given axial speed of test object 110 ($V_{pipe}$), $V_{aperture}$ must be proportionately increased by increasing the measurement cycle pulse repetition frequency (PRF).

It can also been seen by Eq. 1 & 2, that the inspection throughput is a function of the total number of probes, apertures and the rotating speed, rpm.

It should also be noted in FIG. 8a that the unit pipe contour travelling distance 801 is the width of probe $L_{probe}$ plus Δl, which is $V_{pipe} \cdot \Delta t$.

To Achieve 100% Scan Coverage

Figure 8B:
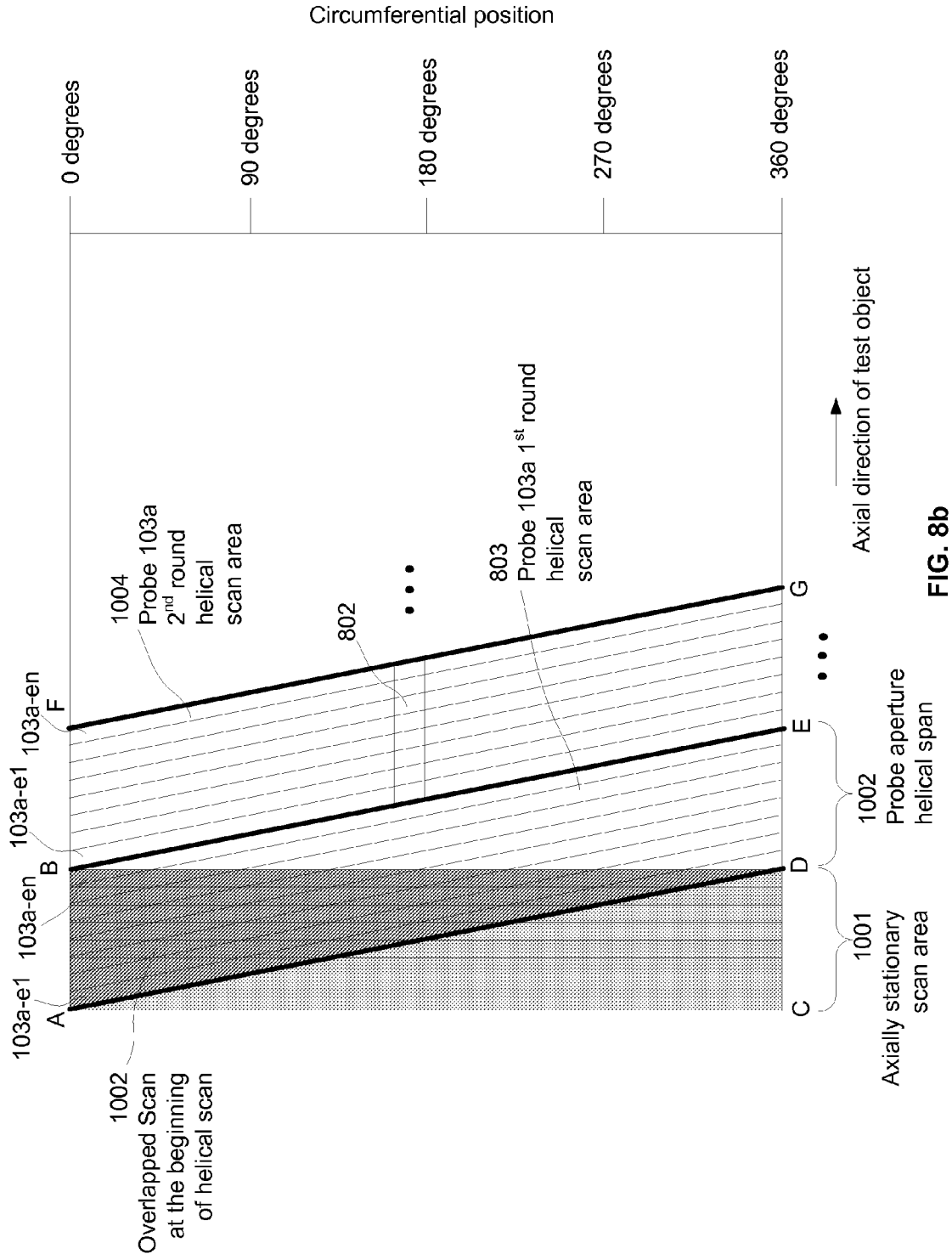
FIG. 8b is a diagram showing the helical scan pattern produced by the rotating phased-array inspection system using one PA probe with eight apertures.

In the forthcoming exemplary case only one probe 103a with only one set of apertures is used, in relation to FIGS. 8a and 8b to describe the helical coverage provided by simple probe scanning. Furthermore, the full surface of the cylindrical test object 110 in FIGS. 8b and 8c is shown as a two-dimensional figure to facilitate illustration and explanation.

As can be seen in FIG. 8a, the first aperture of PA probe 103a includes elements 103a-$e_1$, 103a-e8. For simplicity, only probe 103a is used to make the exemplary case shown in FIG. 8b. A typical test object scanning process providing complete coverage of the test object circumferential surface preferably begins by rotating probe 103a at a known position or velocity around test object 110 at least once while it is in a stationary axial position which results in scan area 1001 in FIG. 8b. Continuing with FIG. 8b, PA probe 103a maintains a constant rotational velocity while the axial movement of test object 110 is brought to a known velocity before entering the helical inspection zone. Helical scan 1002 of PA probe 103a begins at the 0 degree circumferential position denoted by points A and B. This first helical scan ends at the 360 degree circumferential position denoted by points D and E. The second helical scan starts and ends the same way with the respective elements at points B and F, and E and G respectively. The helical scan process continues until the end of the test object is reached.

The inspection system of the present disclosure will typically be used for test objects, such as pipes or rods, that are manufactured by means of an in line process—i.e. a linear arrangement of process steps, including the inspection. Accordingly, the efficiency of the manufacturing process is directly related to test object throughput. The aforementioned embodiment provides complete inspection coverage of the test object circumferential surface; however, the axial motion of the test object 110 must stop momentarily at the beginning of the inspection to accomplish this. If throughput is of paramount concern, test object 110 may enter and move axially through the inspection system in a continuous motion; however, this can only be done at the expense of incomplete inspection coverage on a small portion of the leading extremity of test object 110.

As shown in FIG. 1, the preferred embodiment of the present disclosure employs four PA probes 103. In the forthcoming exemplary arrangement, the probes are disposed in pairs 180 degrees apart (i.e. 103a and c, and 103b and d). A first pair (103a, 103c) is used to perform linear scans with a first inspection incident angle, such as that required for longitudinal wall thickness measurement. A second pair (103b, 103d) is used with a second inspection incident angle, such as that required for transverse flaw detection. It should be noted that any inspection incident angle that probe 103 is capable of employing may be used.

The larger the number of probes 103 used for a given inspection incident angle, the faster the axial speed of test object 110 may be, while maintaining sufficient inspection surface resolution.

It should be appreciated that the present invention is not limited to the use of four PA probe head units on a single rotating plate. Other configurations are possible such as using two PA probe head units positioned at 0 and 180 degrees on rotating plate 108, or with three PA probe head units at 0, 120, 240 degrees. It must also be recognized that one probe head unit can also be used, typically with a counterweight opposite the probe head unit on the rotating plate.

Referring now to FIG. 8c, which shows the interlaced pattern that can be achieved using the probe pair 103a and 103c of FIG. 1. Because both of these probes rotate 360 degrees around the test object at the same time, the axial speed of test object 110 can be twice that of the single rotating probe 103a described above while achieving the same circumferential scanning resolution. As can be seen by comparing FIGS. 8b and 8c, the probe aperture span distance is traversed in 360 degrees and 180 degrees respectively; therefore, for the same rotational speed, it takes probe pair 103a and 103c half the time to cover the same axial distance. Accordingly, the use of a plurality of probes 103 sharing the same incident inspection angle provides the means to increase test object axial throughput in direct proportion to the number of these probes used without sacrificing circumferential scanning resolution.

It should be appreciated that the above descriptions and drawings disclose illustrative embodiments of the invention. Given the benefits of this disclosure, those skilled in the art will appreciate that various modifications, alternate constructions, and equivalents may also be employed to achieve the advantages of the invention.

Although the present invention describes a wireless transmitter/receiver 126 integrated into each data acquisition unit, it must be recognized that a wireless transmitter/receiver for each DAU could be external to the DAUs. It must also be recognized that all of the data acquisitions could potentially share a single wireless transmitter/receiver on the rotating disc.

It must also be recognized that although the preferred embodiment stops the test object at the beginning and end of each inspection to optimize the inspections results at the extremities of the test objects, the present invention is not limited in this respect. Continuous translation movement of the test objects on a conveyor can be applied to the present invention.

It should be noted that the wireless connection 121 described in the present disclosure can include the usage of many types of transmission and reception technologies and communication protocols to achieve signal communication between stationary user operating station 120 and rotating probe assembly 100, including but not limited to radio frequency, microwave, acoustic, infra-red and other optical technologies. Furthermore, many standard or private wireless protocols, such as the Internet protocol (TCP/IP), may be employed. It should also be noted that it is preferable to use private transmission frequency bands due to the slower latency inherent in public frequency bands. For example, conventional public frequency bands used by wireless technology employed in personal computers can have transmission-reception latency in the order of milliseconds due to a large number of users vying for the same public frequency band. Accordingly, the latency period of private frequency bands is much shorter due to a much smaller population of users.

Although the description of the embodiments of the present disclosure is provided for an application using phased-array ultrasonic probes to test cylindrically shaped test objects, its application is not limited in this regard. Indeed, a broad range of multi-element probe sensor arrays may be employed to achieve the benefits of the present disclosure. Examples of such probes are eddy current arrays (ECA) and acoustic probes. It should also be noted that the teachings of the present disclosure may also be applied to single element sensor probes. Furthermore, test objects with non-round axial cross sections, such as oval and polygons, may also be tested.

DETAILED DESCRIPTION OF ALTERNATIVE EMBODIMENTS

The following design variations of the preferred embodiment should be recognized by those skilled in the art to be within the scope of the present disclosure. The detailed description of the following alternative embodiments focuses on the portion of the embodiments differing from the preferred embodiment, and should be construed complementarily to the preferred embodiment.

Alternative Embodiment 1

Referring to FIG. 1, an electrical power generator/distributor 109 is optionally employed in lieu of external power supplied via slip ring interface 705 (in FIGS. 7a & b). As shown in FIG. 1, electrical power is generated for rotating probe assembly 100 by generator 109 mounted on rotating plate 108 with its drive shaft gear 109a engaged with gear 718 of bearing 703 of FIG. 7c. The energy supplied to generator 109 is derived from the rotational kinetic energy provided by rotation drive 704, or 702. Electrical regulator/distributor 109c converts the electrical energy provided by generator 109 to either a direct or alternating current voltage (i.e. DC or AC) appropriate for use with the devices on the rotating plate 108 requiring electrical power, such as Data Acquisition Units (DAU) 102 and battery 109b.

The charging and monitoring device for battery 109b may be located within electrical regulator/distributor 109c or battery 109b. Furthermore, battery 109b (re-chargeable or non-rechargeable) may be used in a stand alone manner without the need for generator 109 or electrical regulator/distributor 109c as long as a means is provided to connect the battery 109b to probe head unit 101 requiring its power. More than one battery may be used, each preferably placed in proximity to the device or devices it powers.

It should be appreciated that existing generators or alternators can be repurposed for the present invention, providing electric power source for the presently disclosed rotating PA system.

Alternative Embodiment 2

In lieu of providing pressurized air for pneumatic cylinder 106 in the manner described above for the preferred embodiment, an on-board air compressor is optionally disposed on rotating plate 108 may be used.

Referring to FIG. 1, alternatively ambient air may be optionally compressed by compressor 112 and in turn provided as the pressurized air source to working source distributor 125. Compressor 112 can be driven by an electric motor or alternatively by the mechanical energy of rotating plate 108 in a similar manner as described above for generator 109.

Further alternatively, a pressurized vessel 113 can be utilized so that compressor 112 can pressurize vessel 113 which would provide pressurized air to coupling ring 700. It should also be noted that the mounting of only pressurized vessel 113 on rotating plate 108 is also sufficient to provide pressurized air to working source distributor 125. In this case, vessel 113 would be filled with compressed air by attaching a stationary compressor during the sessions when rotating plate 108 is stopped.

Alternative Embodiment 3

In lieu of using earlier described couplant ring 700 and couplant interface 706 shown in FIGS. 1 and 7a, b and c, a stationary couplant irrigation conduit 900 is shown in FIGS. 9a and 9b, which is mounted in a fixed position with respect to rotating plate 108 of rotating probe assembly 100. Dispersion nozzles 901a, 901b and others are circumferentially mounted to irrigation conduit 900 to provide a substantially laminar flow of couplant, preferably water, between the sensing surface of probes 103a and 103b and respective inspection surface 902.

Examples of couplant dispersion are shown for dispersion nozzles 901a and 901b (FIG. 9a). Dispersed couplant 904a and 904b is applied to coupling regions 902a and 902b respectively, preferably in direction as shown in the spraying direction of 904 to preferably opposing to the axial feed direction of test object 110 and the direction of rotation of plate 108.

It should be noted that dispersion nozzles 901 are not confined to direction as shown in spraying couplant 904 or a fixed pattern. Indeed, the dispersion direction and pattern may be adjusted manually or dynamically to optimize the laminar flow of couplant on surface 902 of test object 110.

Alternative Embodiment 4

As shown in FIG. 10, an alternative embodiment involves deploying multiple paralleled rotating plates, each of which with PA probe head units installed. The deployment of multiple rotating PA assemblies, such as 100a and 100b allows for increased linear speed of the test object during the inspection. Each of these multiple rotating plate can also have a specific kind of PA probes deployed for a specific inspection task, such as longitudinal and transversal flaw inspection or thickness measurement, etc.

Continuing with FIG. 10, a rotating PA probe assembly carrying base 1003 is used to axially transfer rotating probe assemblies 100a and 100b along the length of test object 110 at the same or different speed. This capability provides the ability to maintain continuous axial movement of test object 110, thereby improving inspection throughput. Carrying base 1003 can also be adjusted in the vertical and lateral direction to compensate for position variations of test object 110. The employment of carrying bases 1003 also enables versatile design of the whole PA inspections system by allowing flexible positioning of multiple groups of rotating probe assemblies with different inspection applications.

The preceding description of the preferred embodiment indicates a preference to have test object 110 to be stopped at its starting and end of a test object, in order to be scanned one or more times of the extremities to ensure that the entire circumferential surface undergoes a complete linear scan as shown in FIG. 3. With this alternative embodiment deployed involving mobile rotating PA assemblies (shown in FIG. 10), at the beginning and the end of a test object, by moving inspection assembly 100a at the same speed and in the same axial direction as test object 110 for one linear scan length, the relative motion between them results in an essentially stationary scan of test object 110, thereby resulting in the same scan results as shown in enclosed area ABCD in FIG. 8b. This enables continuous feeding the plurality of test object with stopping conveyor 1004 and therefore increase inspection throughput.

Alternative Embodiment 5

Figure 11:
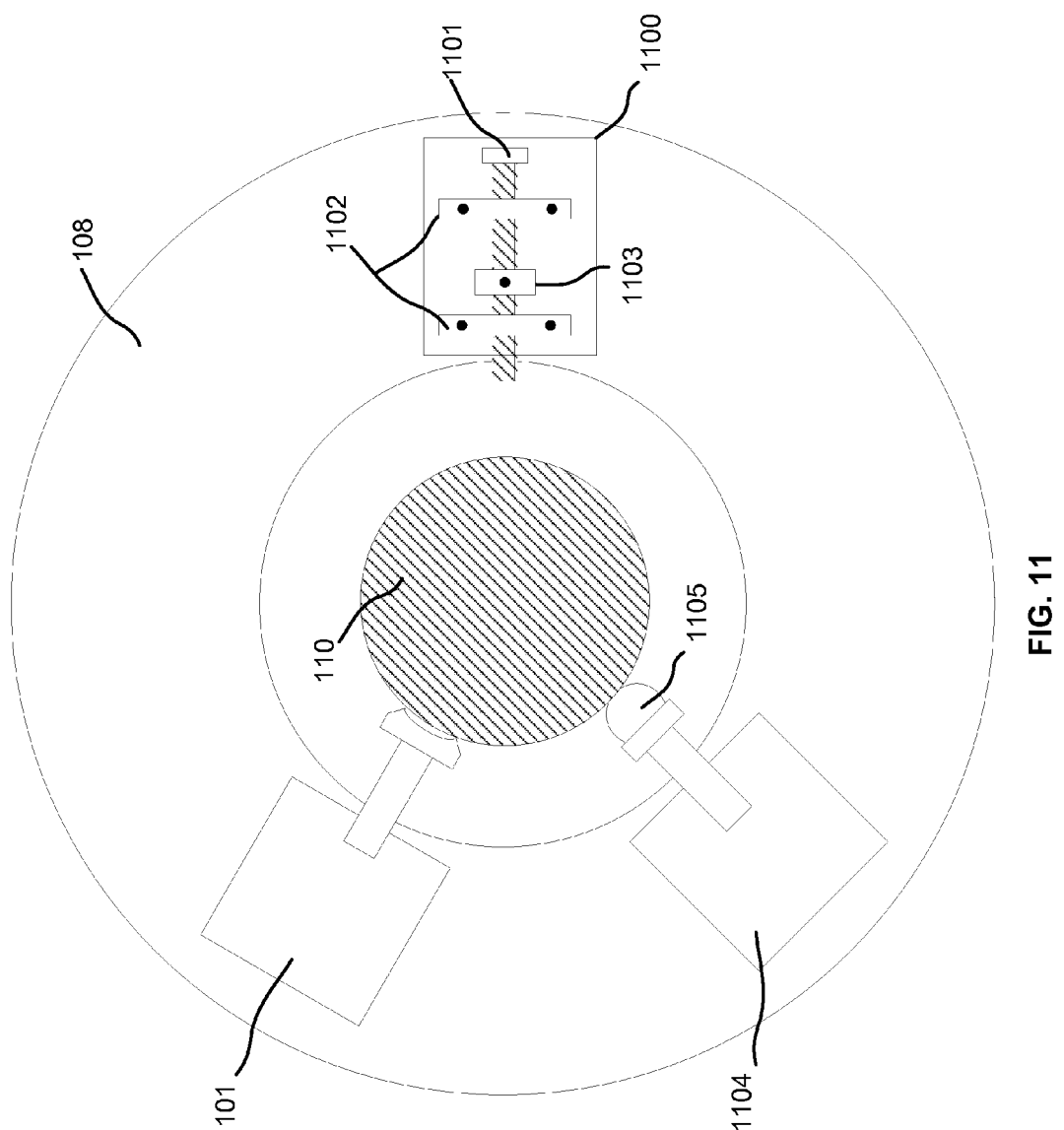
FIG. 11 is a diagram showing an optional device that can be used to adjust the center of mass of the rotating PA probe assembly for optimal rotational stability, and a two-dimensional ball tracking device for keeping track of the location of probe inspection measurements with respect to the circumferential and axial position on the test object.

Referring collectively to FIG. 11 and FIG. 1, alternatively the circumferential and axial position of probes 103 with respect to the contour of test object 110 are tracked by a position tracking device 1105 affixed to its housing 1104 or integrated with mounting yokes 105 (FIG. 2) or other suitable location on mounting plate 108. Position tracking device 1105 is operably coupled to the inspection surface of test object 110. The signals from device 1105 are provided to Data Acquisition Unit (DAU) 102, or to the electronics within housing 1104, to send information of circumferential and axial position of probe 103 with respect to test object 110 to user operating station 120 by a wireless interface or slip ring connection described above.

Alternative Embodiment 6

Continuing to refer to FIG. 11 and FIG. 1, optionally an embodiment providing a means to adjust the center of mass of rotating plate 108 with a non-symmetrical mass arrangement of probe heads and other equipment is shown in FIG. 11. Specifically, a mass adjustment device 1100 is located on rotating plate 108 in a region with lower mass than the radial opposing side where PA probe unit 101 and position tracing device 1105 are located. One or more weights 1103 are located at a fixed position on an adjustment screw 1101. The radial position of weight 1103 may be manually or automatically adjusted to set the location of the center of mass of rotating plate 108. This is accomplished by measuring at a known circumferential position on the side leaning weight of rotating plate 108 by a balance sensor 717 of FIG. 7a that is located on one of the two vertical support members of frame 701.

The weight is measured at preferably four 90 degree rotational intervals, after which rotating plate 108 is rotated to the location where the maximum weight was measured. Then, screw 1101 is turned counterclockwise, for example, a predetermined amount to displace weight 1103 radial outward. Next, balance sensor 717 indicates the new weight and then plate 108 is rotated and the weighed again at 90 degree intervals as described above. This process continues until a weight measurement inflection point occurs—meaning that sensor 717 indicates, for example, an increase in the measured weight after having indicated for the prior weighing cycle a decrease in the measured weight. The weighing process may further continue one or more times by adjusting screw 1301 to a lesser degree resulting in a smaller weight increment change. The center of mass balancing process ends when the last weight measurement inflection point occurs with the finest displacement of weight 1103.

The exemplary center of mass balancing process described above may be implemented in a number of different ways by those skilled in the art.

Alternative Embodiment 7

More than one rotating probe may be longitudinally disposed at a given circumferential position on rotating plate 108 and be operated in unison. When there are two probes disposed along axial line with their linear array aperture spans contiguous to each other, the pipe can travel two probe lengths during one rotating cycle time T. If the pipe is fed with an axial move faster then $2L_{probe}/T$, there will be un-scanned helical gap left behind the scanned area.

Consequently, when there are n probes dedicated to the same type of defect or wall thickness inspection disposed along axial line contiguous to each other, the pipe can travel n probe lengths during on rotating cycle time T.

That is to say, in order to achieve 100% scan coverage, the longitudinal speed that the pipe is fed is constrained by the following equation Eq. 3, given m as the total number of probes disposed contiguous to each other axially, $V\text{pipe} \cdot T/L\text{probe} = V\text{pipe} \cdot 60/(L\text{probe} \cdot \text{rpm}) \leq m$ or $$m \geq V\text{pipe} \cdot T/L\text{probe} = V\text{pipe} \cdot 60/(L\text{probe} \cdot \text{rpm}) \qquad \text{Eq. 3}$$

The exemplary helical scans shown in FIGS. 10 and 11 may be also be obtained by moving rotating probe assembly 1201 along the axial length of a completely stationary test object 110.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. An inspection system for performing non-destructive testing of test object, the inspection system comprising:
    a test object conveyor for conveying the test object along a longitudinal conveyance path;
    at least one probe assembly further including at least one phased-array probe, the phased-array probe being configured to send ultrasonic beams to the test object and to sense echo signals induced in the test object and convert the echoes to electronic response data and a probe assembly conveyor configured to movably support the probe assembly, to move the probe assembly on a circumferential path about the test object;

at least one data acquisition unit disposed on the probe assembly conveyor which acquires the response data from the phased-array probe, provides phased array firing command to the phased-array probe in order to apply desired focus angles for the ultrasonic beams for the testing and perform a first part of data processing including producing real-time A-scan data;

a control and data processing system coupled to the test object conveyor and to the probe assembly conveyor and the data acquisition unit, the processing system configured to send command to the data acquisition unit, receive and provide a second part of data processing received from the data acquisition unit while, simultaneously while the test object moves along the longitudinal path and the phased-array probes move on the circumferential path.

2. The inspection system of claim 1, wherein the probe assembly comprises at least two phased-array probes, which are longitudinally juxtaposed to one another on said probe assembly conveyor.

3. The inspection system of claim 2, including a couplant irrigation source for coupling couplant fluid from a first to a second bearing structure, and including couplant fluid dispersants located adjacent the at least two phased-array probes.

4. The inspection system of claim 3, wherein the couplant dispersants are configured to generate a substantial laminar flow of couplant between an outer surface of a water wedge coupled to the phased-array probes and an opposing surface of the test object.

5. The inspection system of claim 2, including a pressurized gas source for coupling a pressurized gas from a first to a second bearing structure, and including pressurized gas dispersants located adjacent to the at least two phased-array probes.

6. The inspection system of claim 5, wherein the probe assembly conveyor is configured to rotate the probe assembly around the longitudinal path at a substantially constant rotational speed.

7. The inspection system of claim 2, including a pressurized gas source, and including pressurized gas dispersants located adjacent to the at least two phased-array probes.

8. The inspection system of claim 1, including at least one circumferential position sensor acquiring data regarding circumferential position of the phased-array probe, and at least one longitudinal position sensor acquiring data regarding the test object's longitudinal position.

9. The inspection system of claim 8, wherein the first part of the data processing is produced by the data acquisition unit as real-time A-scan data based on the sensed signals by the phased-array probe, the data regarding the longitudinal position and the data regarding the circumferential position.

10. The inspection system of claim 9, including at least one predetermined gate or threshold for determining when sensed signals indicate a flaw in the A-scan data.

11. The inspection system of claim 10, including a warning and marking mechanism providing the longitudinal and circumferential positions of the flaw that is detected.

12. The inspection system of claim 1, referring to FIG. 8a, wherein, the test object conveyor is effective to convey the test object over axial distances including the axial distance $\Delta l$ during the time of $\Delta t$, the probe assembly conveyor and the phased-array probe are operated according to following Eq. 1

$$V_{pipe} \leq m \cdot L_{probe}/T = m \cdot L_{probe} \cdot (rpm)/60 \text{ (m/s)} \qquad \text{Eq. 1}$$

and wherein,
a) $L_{probe}$ is defined as a probe aperture span which is the distance between a given element position in a first aperture and a respective element position in a last aperture;
b) $\Delta t$ is defined as a scan cycle time, which begins at the start of a pulse-receive cycle of the phased-array probe for the first aperture and ends at the completion of a pulse-receive cycle for the last aperture =;
c) $V_{pipe}$ is a constant, and is the speed that test object is fed;
d) $\Delta l$ is an axial distance that the pipe travels during $\Delta t$;
e) rpm is the rotating speed of the rotating probe assembly conveyor;
f) T is the time it takes for the phased-array probe to rotate 360 degrees around test object, which is $rpm^{-1}$;
g) $V_{aperture}$ is a constant and is the speed of the phased-array probe head of each aperture scan cycle;
h) $V_{rotate}$ is an angular speed of the rotating probe assembly conveyor;
i) n is the number of apertures of each PA probe;
j) m is the total number of probes disposed on the probe assembly conveyor; and
k) $\Delta y$ is a unit circumferential scan resolution.

13. The inspection system of claim 12, wherein $\Delta y$ is determined by Eq. 2:

$$\Delta y = V_{aperture} \cdot \Delta t/n = 2\pi R \cdot rpm \cdot \Delta t/n \qquad \text{Eq. 2}$$

wherein R is the radius of the test object.

14. The inspection system of claim 1, wherein the probe assembly comprises at least two phased-array probes of a first type, which are circumferentially juxtaposed to one another on said probe assembly conveyor and are configured to optimize sensing of structural cracks or faults of the test object generally extending in the longitudinal path.

15. The inspection system of claim 1, wherein the probe assembly comprises at least two phased-array probes of a second type, which are circumferentially juxtaposed to one another on said probe assembly conveyor and are configured to optimize sensing of cracks or faults generally extending at a substantial angle to the longitudinal path.

16. The inspection system of claim 1, wherein the probe assembly comprises:
at least two phased-array probes of a first type, and at least two phased-array probes of a second type.

17. The inspection system of claim 1, wherein the test object conveyor is configured and controlled to carry the test object at a known speed along said longitudinal conveyance path throughout substantially the entirety of the longitudinal path.

18. The inspection system of claim 1, including a wireless system for wirelessly communicating data signals from the probe assembly to a processing computer.

19. The inspection system of claim 1, wherein the at least one phased array probe senses the longitudinal position of the test object.

20. The inspection system of claim 1, wherein the probe assembly conveyor is constructed and configured to enable rotational movement of the phased-array probes over an angular range substantially including 0° to 360° about the longitudinal path.

21. The inspection system of claim 1, wherein the assembly probe conveyor includes a position adjuster which is configured to control a spacing provided between the phased-array probes and the test object.

22. The inspection system of claim 1, including a mechanism for rotating the test object and for adjusting a center of mass thereof.

23. The inspection system of claim 1, wherein the probe assembly conveyor is effective to move the probe assembly at the same axial speed as the test object for testing an initial test object section.

24. The inspection system of claim 1, wherein the control system includes a computer program which is configured to store maximum linear and rotational speed values for the test object and for the phased-array probes.

25. The inspection system of claim 1, wherein the phased-array probes comprise acoustical transducers.

26. The inspection system of claim 1, wherein the phased-array probes comprise elements that are configured to induce and sense Eddy Currents in the test object.

27. The inspection system of claim 1, including an electrical generator mounted to the probe assembly conveyor and configured to generate electrical power for the probe assembly.

28. The inspection system of claim 1, including a stationary couplant irrigation assembly which sprays couplant to each of the at least one of the probe in such a way that the couplant forms a laminate layer between the surface of the test object and a test surface of the probe facing the surface of the test object.

29. An inspection system for performing non-destructive testing of test object, the inspection system comprising:
- a test object conveyor for conveying the test object along a longitudinal conveyance path;
    - at least one probe assembly further including at least one phased-array probe, the phased-array probe being configured to send ultrasonic beams to the test object and to sense echo signals induced in the test object and convert the echoes to electronic response data and a probe assembly conveyor configured to movably support the probe assembly, to move the probe assembly on a circumferential path about the test object;
- at least one data acquisition unit disposed on the probe assembly conveyor which acquires the response data from the phased-array probe, provides phased array firing commands to the phased-array probe in order to apply desired focus angles for the ultrasonic beams for the testing and perform a first part of data processing including producing real-time A-scan data;
- a control and data processing system coupled to the test object conveyor and to the probe assembly conveyor configured to allow data acquisition by and from the phased-array probes while, simultaneously, the test object moves along the longitudinal path and the phased-array probes move on the circumferential path, wherein the probe assembly conveyor includes a first stationary bearing structure which rotatably supports a second rotatable bearing structure, the second bearing structure being configured to support the probe assembly.

30. The inspection system of claim 29, including an electrical coupling structure for coupling electric power and signals between the first bearing structure and the second bearing structure.

31. The inspection system of claim 30, wherein the electrical coupling structure comprises a slip ring cavity.

* * * * *